United States Patent
Ramsey et al.

(10) Patent No.: US 10,471,428 B2
(45) Date of Patent: Nov. 12, 2019

(54) FLUIDIC DEVICES WITH NANOSCALE MANIFOLDS FOR MOLECULAR TRANSPORT, RELATED SYSTEMS AND METHODS OF ANALYSIS

(71) Applicant: The University of North Carolina at Chapel Hill, Chapel Hill, NC (US)

(72) Inventors: John Michael Ramsey, Chapel Hill, NC (US); Laurent D. Menard, Raleigh, NC (US); Michael A. Tycon, San Jose, CA (US); Oscar A. McCrate, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 15/568,980

(22) PCT Filed: May 4, 2016

(86) PCT No.: PCT/US2016/030702
§ 371 (c)(1),
(2) Date: Oct. 24, 2017

(87) PCT Pub. No.: WO2016/182811
PCT Pub. Date: Nov. 17, 2016

(65) Prior Publication Data
US 2018/0126379 A1    May 10, 2018

Related U.S. Application Data

(60) Provisional application No. 62/159,503, filed on May 11, 2015.

(51) Int. Cl.
*B01L 3/00* (2006.01)
*G01N 15/14* (2006.01)
*G01N 15/00* (2006.01)

(52) U.S. Cl.
CPC .... *B01L 3/502761* (2013.01); *G01N 15/1463* (2013.01); *G01N 15/1484* (2013.01);
(Continued)

(58) Field of Classification Search
None
See application file for complete search history.

(56) References Cited

U.S. PATENT DOCUMENTS

| | | | |
|---|---|---|---|
| 5,498,392 A | 3/1996 | Wilding et al. | |
| 5,858,187 A | 1/1999 | Ramsey et al. | |

(Continued)

FOREIGN PATENT DOCUMENTS

| | | |
|---|---|---|
| JP | 2003-166934 | 6/2003 |
| JP | 2005-102619 | 4/2005 |

(Continued)

OTHER PUBLICATIONS

Extended European Search Report corresponding to European Patent Application No. 16793201.1 (9 pages) (dated Oct. 9, 2018).
(Continued)

*Primary Examiner* — Joseph G. Dauner
(74) *Attorney, Agent, or Firm* — Myers Bigel, P.A.

(57) ABSTRACT

Fluidic devices with a primary transport nanochannel(s) intersected by at least one nanoscale manifold for active control of capture, manipulation and transport of analyte molecules. The at least one manifold can be an array or network of nanochannels, nanoslits or nanoelectrodes joined to a common voltage or pressure source. A respective nanoscale manifold can be configured to allow for precise and active control of driving forces applied to the primary transport nanochannel(s) to drive molecular transport through the various regions along the transport nanochannel(s). The at least one manifold can generate monotonic force gradients with a limited or reduced number (Continued)

of independent input potentials and/or pressures applied to the device.

30 Claims, 21 Drawing Sheets

(52) U.S. Cl.
CPC ............... *B01L 2300/0645* (2013.01); *B01L 2300/0816* (2013.01); *B01L 2300/0864* (2013.01); *B01L 2300/0867* (2013.01); *B01L 2300/0896* (2013.01); *B01L 2400/0421* (2013.01); *G01N 15/1459* (2013.01); *G01N 2015/0038* (2013.01)

(56) References Cited

U.S. PATENT DOCUMENTS

| | | | |
|---|---|---|---|
| 5,872,010 A | 2/1999 | Karger et al. | |
| 6,235,471 B1 | 5/2001 | Knapp et al. | |
| 6,524,456 B1 | 2/2003 | Ramsey et al. | |
| 6,540,895 B1 | 4/2003 | Spence et al. | |
| 6,790,671 B1 | 9/2004 | Austin et al. | |
| 6,803,568 B2 | 10/2004 | Bousse et al. | |
| 7,033,474 B1 | 4/2006 | Dubrow et al. | |
| 7,465,381 B2 | 12/2008 | Lopez et al. | |
| 7,670,770 B2 | 3/2010 | Chou et al. | |
| 7,744,762 B2 | 6/2010 | Lazar | |
| 7,960,105 B2 | 6/2011 | Schwartz et al. | |
| 8,246,799 B2 | 8/2012 | Oliver et al. | |
| 8,333,934 B2 | 12/2012 | Cao et al. | |
| 8,691,588 B2 | 4/2014 | Park et al. | |
| 8,722,327 B2 | 5/2014 | Cao et al. | |
| 8,735,065 B2 | 5/2014 | Craighead et al. | |
| 8,764,968 B2 | 7/2014 | Afzali-Ardakani et al. | |
| 9,061,901 B2 | 6/2015 | Cao et al. | |
| 2002/0000516 A1 | 1/2002 | Schultz et al. | |
| 2002/0061529 A1 | 5/2002 | Bridgham et al. | |
| 2002/0072243 A1 | 6/2002 | Craighead et al. | |
| 2002/0081744 A1 | 6/2002 | Chan et al. | |
| 2002/0160365 A1 | 10/2002 | O'Brien | |
| 2002/0190204 A1 | 12/2002 | Hofstadler et al. | |
| 2002/0197603 A1 | 12/2002 | Chow et al. | |
| 2003/0146377 A1 | 8/2003 | Miller et al. | |
| 2004/0033515 A1 | 2/2004 | Cao et al. | |
| 2004/0166504 A1 | 8/2004 | Rossier et al. | |
| 2005/0023156 A1 | 2/2005 | Ramsey et al. | |
| 2005/0082204 A1 | 4/2005 | Schwartz et al. | |
| 2005/0103713 A1 | 5/2005 | Ramsey et al. | |
| 2005/0196746 A1 | 9/2005 | Xu et al. | |
| 2006/0084078 A1 | 4/2006 | Zhao | |
| 2006/0169587 A1 | 8/2006 | Lopez et al. | |
| 2006/0240573 A1 | 10/2006 | Kao et al. | |
| 2006/0275778 A1 | 12/2006 | Wu et al. | |
| 2006/0278879 A1 | 12/2006 | Busta | |
| 2007/0057179 A1 | 3/2007 | Bousse et al. | |
| 2007/0145263 A1 | 6/2007 | Weng | |
| 2007/0192911 A1 | 8/2007 | Jin et al. | |
| 2008/0057192 A1 | 3/2008 | Faguet | |
| 2009/0023146 A1 | 1/2009 | Harnack et al. | |
| 2009/0111115 A1 | 4/2009 | Drmanac et al. | |
| 2009/0115094 A1 | 5/2009 | Chou et al. | |
| 2009/0136682 A1 | 5/2009 | Branton et al. | |
| 2009/0305273 A1 | 12/2009 | Cao et al. | |
| 2010/0029508 A1 | 2/2010 | Austin et al. | |
| 2010/0075428 A1 | 3/2010 | Wang et al. | |
| 2010/0159462 A1 | 6/2010 | Takayama et al. | |
| 2011/0036994 A1 | 2/2011 | Frayling | |
| 2011/0076735 A1 | 3/2011 | Jovanovich et al. | |
| 2011/0201509 A1 | 8/2011 | Tegenfeldt et al. | |
| 2011/0226623 A1 | 9/2011 | Timp et al. | |
| 2011/0227558 A1 | 9/2011 | Mannion et al. | |
| 2011/0296903 A1* | 12/2011 | Cao ............... B01L 3/502761 73/64.56 | |
| 2011/0308949 A1 | 12/2011 | Afzali-Ardakani et al. | |
| 2012/0193231 A1 | 8/2012 | Afzali-Ardakani et al. | |
| 2012/0196376 A1 | 8/2012 | Park et al. | |
| 2013/0068618 A1 | 3/2013 | Harrer et al. | |
| 2013/0195723 A1 | 8/2013 | Ramsey et al. | |
| 2013/0224736 A1 | 8/2013 | Marie et al. | |
| 2013/0341190 A1 | 12/2013 | Quake et al. | |
| 2014/0194313 A1 | 7/2014 | Craighead et al. | |
| 2014/0194314 A1 | 7/2014 | Walsworth et al. | |
| 2014/0197105 A1 | 7/2014 | DiBiasio et al. | |
| 2014/0238856 A1 | 8/2014 | Ramsey et al. | |
| 2014/0249039 A1 | 9/2014 | Cao et al. | |
| 2014/0272958 A1 | 9/2014 | Ramsey et al. | |
| 2015/0008124 A1 | 1/2015 | Oliver | |
| 2016/0024569 A1 | 1/2016 | Ramsey et al. | |

FOREIGN PATENT DOCUMENTS

| | | | |
|---|---|---|---|
| JP | 2007-149861 | 6/2007 | |
| WO | WO 96/04547 A1 | 2/1996 | |
| WO | WO 2000/002038 A1 | 1/2000 | |
| WO | WO 01/13088 A1 | 2/2001 | |
| WO | WO 03/025540 A2 | 3/2003 | |
| WO | WO 2007/011622 A2 | 1/2007 | |
| WO | WO 2008/079169 A2 | 7/2008 | |
| WO | WO 2008/132734 A2 | 11/2008 | |
| WO | WO 2009/030953 A1 | 3/2009 | |
| WO | WO 2009/052214 A2 | 4/2009 | |
| WO | WO 2009/120642 | 10/2009 | |
| WO | WO-2011150475 A1 * | 12/2011 | ........... C12Q 1/6841 |
| WO | WO 2012/040098 A2 | 3/2012 | |
| WO | WO 2012/055415 | 5/2012 | |
| WO | WO 2012/170560 A2 | 12/2012 | |
| WO | WO 2013/039778 | 3/2013 | |
| WO | WO 2013/088098 A2 | 6/2013 | |
| WO | WO 2013/119765 A1 | 8/2013 | |
| WO | WO 2013/176767 A1 | 11/2013 | |
| WO | WO 2013/191908 A1 | 12/2013 | |

OTHER PUBLICATIONS

Abgrall et al. "Nanofluidic Devices and Their Applications" *Anal. Chem.* 80:2326-2341 (2008).
Ai et al. "Field Effect Regulation of DNA Translocation through a Nanopore" *Analytical Chemistry* 82(19):8217-8225 (2010).
Alkan et al. "Genome structural variation discovery and genotyping" *Nat. Rev. Genet.* 12:363-376 (2011).
Allison et al. "Direct atomic force microscope imaging of EcoRI endonuclease site specifically bound to plasmid DNA molecules" *Proc. Natl. Acad. Sci. USA*, vol. 93, pp. 8826-8829, Aug. 1996, Applied Biological Sciences.
Apel et al. "Diode-like single-ion track membrane prepared by electro□stopping", *Nucl. Instrum. Methods Phys. Res.*, Sect. B, 2001, 184, 337-346.
Baday et al. "Multicolor super-resolution DNA imaging for genetic analysis", *Nano Lett.*, 2012, vol. 12, pp. 3861-3866.
Balducci et al. "Double-Stranded DNA Diffusion in Slitlike Nanochannels" *Macromolecules* 39:6273-6281 (2006).
Balducci et al. "Conformational preconditioning by electrophoresis of DNA through a finite obstacle array" *Macromolecules* 41:5485-5492 (2008).
Brochard et al. "Dynamics of confined polymer chains", J. Chem. Phys., Jul. 1977, vol. 67, pp. 52-56.
Brochard-Wyart et al. "Dynamics of Taut DNA chains", *Europhys. Lett.*, 1999, vol. 47(2), pp. 171-174.
Campbell et al. "Electrophoretic manipulation of single DNA molecules in nanofabricated capillaries", *Lab Chip*, 2004, 4:225-229.
Cao et al. "Fabrication of 10 nm enclosed nanofluidic channels", *Applied Physics Letters*, 81(1):174-176 (2002).
Cao et al., "Gradient nanostructures for interfacing microfluidics and nanofluidics", *Appl. Phys. Lett.*, Oct. 14, 2002; vol. 81, No. 16, pp. 3058-3060.
Chantiwas et al., "Flexible fabrication and applications of polymer nanochannels and nanoslits", *Chem. Soc. Rev.*, 2011, vol. 40, pp. 3677-3702.

(56) References Cited

OTHER PUBLICATIONS

Chou et al., "A microfabricated device for sizing and sorting DNA molecules", *Proc. Natl. Acad. Sci.*, 1999, vol. 96, pp. 11-13.
Cipriany et al., "Single molecule epigenetic analysis in a nanofluidic channel", Anal. Chem., Mar. 15, 2010, vol. 82, No. 6, pp. 2480-2487.
Craddock et al., "Genome-wide association study of CNVs in 16,000 cases of eight common diseases and 3,000 shared controls", *Nature*, 2010, vol. 464, pp. 713-720.
Craighead et al. "Future lab-on-a-chip technologies for interrogating individual molecules" Nature 2006, 442, 387.
Cross et al. "Size-dependent DNA mobility in nanochannels", *Journal of Applied* Physics, 2007, vol. 102, pp. 024701-1-024701-5.
Cui, S.T., "Counterion-Hopping along the Backbone of Single-Stranded DNA in Nanometer Pores: A Mechanism for Current Conduction", *Physical Review Letters*, 2007, vol. 98, pp. 138101-1-138101-4.
Das et al., "Single molecule linear analysis of DNA in nano-channel labeled with sequence specific fluorescent probes", *Nucl. Acids Res.*, 2010, vol. 38, e177, 8 pages.
Dimalanta et al., "A microfluidic system for large DNA molecule arrays", *Anal. Chem.*, 2004, vol. 76, pp. 5293-5301.
Douville et al., "DNA linearization through confinement in nanofluidic channels", *Anal Bioanal Chem.*, 2008, vol. 391, pp. 2395-2409.
Duke et al. "Microchips for Sorting DNA" pp. 11-26 (1997).
Eijkel et al. "Nanofluidics: what is it and what can we expect from it?" Microfluid. Nanofluid. 2005, 1, 249.
Extended European Search Report corresponding to European Patent Application No. 14778772.5 (15 pages) (dated Feb. 7, 2017).
Fan et al. "DNA Translocation in Inorganic Nanotubes", *Nano Letters*, vol. 5, No. 9, Sep. 2005, 1633-1637.
Fischbein et al. "Sub-10 nm Device Fabrication in a Transmission Electron Microscope" Nano Letters 2007, vol. 7, 1329.
Foquet et al., "DNA fragment sizing by single molecule detection in submicrometer-sized closed fluidic channels", *Anal. Chem.*, 2002, vol. 74, pp. 1415-1422.
Freitag et al., "Meandering nanochannels for imaging of ultra-long DNA molecules", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, pp. 1758-1760.
Gierhart et al. "Nanopore with transverse nanoelectrodes for electrical characterization and sequencing of DNA" Sens. and Actuators B 2008, 132, 593.
Gierak et al. "Sub-5 nm FIB direct patterning of nanodevices", *Microelectronic Engineering*, 2007, vol. 84, pp. 779-783.
Han et al., "Prediction of nanopattern topography using two-dimensional focused ion beam milling with beam irradiation intervals", *Microelectronic Engineering*, 2010, vol. 87, pp. 1-9.
Han et al., "Separation of long DNA molecules in a microfabricated entropic trap Array", *Science*, May 12, 2000; vol. 288, No. 5468, pp. 1026-1029.
Haneveld et al., "Wet anisotropic etching for fluidic 1D nanochannels", *J. Micromech. Microeng.*, 2003, vol. 13, pp. S62-S66.
Holzer et al., "Three-dimensional analysis of porous $BaTiO_3$ ceramics using FIB nanotomography", *Journal of Microscopy*, vol. 216, Pt. 1, Oct. 2004, pp. 84-95.
Huh et al., "Tuneable elastomeric nanochannels for nanofluidic manipulation", *Nature Materials*, vol. 6, Jun. 2007, pp. 424-428.
International Search Report and the Written Opinion of the International Searching Authority corresponding to International Patent Application No. PCT/US2014/023371 (16 pages) (dated Jul. 3, 2014).
International Search Report and the Written Opinion of the International Searching Authority corresponding to International Patent Application No. PCT/US2016/030702 (16 pages) (dated Aug. 17, 2016).
Jo et al. "A single-molecule barcoding system using nanoslits for DNA analysis" *Proc. Natl. Acad. Sci*.104(8):2673-2678 (2007).
Jo et al. "Elongation and migration of single DNA molecules in microchannels using oscillatory shear flows" *Lab on a Chip* 9:2348-2355 (2009).
Kasianowicz et al. "Nanoscopic Porous Sensors" *Annu. Rev. Anal. Chem.* 1:737-766 (2008).
Kim et al., "A highly annotated whole-genome sequence of a Korean individual", *Nature*, 2009, vol. 460, pp. 1011-1015.
Kim et al., "Design and numerical simulation of a DNA electrophoretic stretching device", *Lab Chip*, 2007, vol. 7, pp. 213-215.
Kovarik et al., "Nanofluidics in Lab-on-a-Chip Devices", *Anal. Chem.*, 2009, vol. 81, No. 17, pp. 7133-7140.
Kumar et al., "Origin of translocation barriers for polyelectrolyte chains", J. Chem. Phys. 2009, vol. 131, pp. 194903-1-194903-18.
Lagerqvist et al. "Fast DNA Sequencing via Transverse Electronic Transport", *Nano Letters*, 2006, vol. 6, No. 4, pp. 779-782.
Lam et al., "Genome mapping on nanochannel arrays for structural variation analysis and sequence assembly", *Nat. Biotech.*, Aug. 2012, vol. 30, No. 8, pp. 771-776.
Larson et al., "Single DNA molecule stretching in sudden mixed shear and elongational microflows", *Lab Chip*, 2006, vol. 6, Issue 9, pp. 1187-1199.
Lerman et al., Communications to the Editor "Why Does the Electrophoretic Mobility of DNA in Gels Vary with the Length of the Molecule?" Biopolymers 1982, 21, 995-997.
Levy et al. "Entropic Unfolding of DNA Molecules in Nanofluidic Channels" *Nano Letters* 8:3839 (2008).
Levy et al. "DNA manipulation, sorting, and mapping in nanofluidic systems" *Chem Soc Rev* 39(3):1133-1152 (2010).
Li et al., "Focused ion beam fabrication of silicon print masters", *Nanotechnology*, 2003, vol. 14, pp. 220-223.
Li et al. "Sacrificial polymers for nanofluidic channels in biological applications" Nanotechnology 2003, 14, 578.
Liang et al. "Single Sub-20 nm Wide, Centimeter-Long Nanofluidic Channel Fabricated by Novel Nanoimprint Mold Fabrication and Direct Imprinting" *Nano Letters* 7:3774 (2007).
Liang et al. "Nanogap detector inside nanofluidic channel for fast real-time label-free DNA analysis" *Nano Letters* 8(5):1472-1476 (2008).
Lim et al. "DNA methylation profiling in nanochannels" *Biomicrofluidics*, 2011, vol. 5, 034106, 9 pages.
Lugstein et al., "FIB processing of silicon in the nanoscale regime", *Applied Physics A*, 2003, vol. 76, pp. 545-548.
Maleki et al., "A nanofluidic channel with embedded transverse nanoelectrodes", *Nanotechnology*, 2009, vol. 20:105302, pp. 1-6.
Mannion et al., "Conformational analysis of single DNA molecules undergoing entropically induced motion in nanochannels", *Biophys. J.*, 2006, vol. 90, pp. 4538-4545.
Mao et al. "Fabrication and characterization of 20 nm planar nanofluidic channels by glass-glass and glass-silicon bonding" Lab Chip 2005, 5, 837.
Marie et al., Nanofluidic devices towards single DNA molecule sequence mapping, Journal of Biophotonics, 2012, pp. 673-686, vol. 5, No. 8-9.
Mark et al., "Microfluidic lab-on-a-chip platforms: requirements, characteristics and applications", *Chem. Soc. Rev.*, 2010, vol. 39, pp. 1153-1182.
McCarroll et al., "Copy-number variation and association studies of human disease", *Nat. Genet.*, 2007, vol. 39, pp. S37-S42.
McCarthy et al., "Microduplications of 16p11.2 are associated with schizophrenia", *Nat. Genet.*, 2009, vol. 41, No. 11, pp. 1223-1227.
Menard et al. "Analysis of Single DNA Molecules Translocating Through Nanochannels Fabricated in $SiO_2$" *Twelfth International Conference on Miniaturized Systems for Chemistry and Life Sciences* (4 pages) (2008).
Menard et al. "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.
Menard et al. "Fabrication of Sub-5 nm Nanochannels in Insulating Substrates Using Focused Ion Beam Milling" *Nano Letters* 11(2):512-517 (2011).

(56) References Cited

OTHER PUBLICATIONS

Menard et al. "A Device for Performing Lateral Conductance Measurements on Individual Double-Stranded DNA Molecules" *ACS Nano* 6(10):9087-9094 (2012).
Menard et al. "Electrokinetically-Driven Transport of DNA Through Focused Ion Beam Milled Nanofluidic Channels" *Anal. Chem.* 85:1146-1153 (2013).
Mijatovic et al., "Technologies for nanofluidic systems: top-down vs. bottom-up—a review", *Lab Chip*, 2005, vol. 5, pp. 492-500.
Mills et al., "Mapping copy No. variation by population-scale genome sequencing", *Nature*, 2011, vol. 470, pp. 59-65.
Nakayama et al., "Stability and Schottky barrier of silicides: First-principles study", *Microelectronic Engineering*, 2009, vol. 86, pp. 1718-1721.
Nikoobakht, B., "A Scalable Platform for Integrating Horizontal Nanochannels with Known Registries to Microchannels", *Chem. Mater.*, 2009, vol. 21, pp. 27-32.
Orloff et al., "Fundamental limits to imaging resolution for focused ion beams", *Journal of Vacuum Science & Technology B*, Nov./Dec. 1996, vol. 14, No. 6, pp. 3759-3763.
Pang et al. "Fixed-Gap Tunnel Junction for Reading DNA Nucleotides" *ACS Nano* 8(12):11994-12003 (2014).
Perry et al. "Ion transport in nanofluidic funnels" *ACS Nano*, 2010, vol. 4, No. 7, pp. 3897-3902.
Perry et al., "Review of fabrication of nanochannels for single phase liquid flow", *Microfluid Nanofluid*, 2006, vol. 2, pp. 185-193.
Persson et al. "Confinement spectroscopy: probing single DNA molecules with tapered nanochannels" *Nano Letters* 9(4):1382-1385 (2009).
Pinard et al., "Assessment of whole genome amplification-induced bias through high-throughput, massively parallel whole genome sequencing", *BMC Genomics*, 2006, vol. 7, 216, 21 pages.
Pinkel et al., "Comparative genomic hybridization", *Annu. Rev. Genomics Hum. Genet.*, 2005, vol. 6, pp. 331-354.
Pinto et al., "Functional impact of global rare copy No. variation in autism spectrum disorders", *Nature*, 2010, vol. 466, pp. 368-372.
Randall et al., "Methods to electrophoretically stretch DNA: microcontractions, gels, and hybrid gel-microcontraction devices", *Lab Chip*, 2006, vol. 6, pp. 516-525.
Randolph et al., "Focused, Nanoscale Electron-Beam-Induced Deposition and Etching", *Critical Reviews in Solid State and Materials Sciences*, 2006, 31:3, pp. 55-89.
Reccius et al., "Conformation, length, and speed measurements of electrodynamically stretched DNA in nanochannels", *Biophys. J.*, Jul. 2008, vol. 95, pp. 273-286.
Reisner et al. "Statics and Dynamics of Single DNA Molecules Confined in Nanochannels" *Physical Review Letters* 94:196101-1-196101-4 (2005).
Reisner et al. "Nanoconfinement-Enhanced Conformational Response of Single DNA Molecules to Changes in Ionic Environment" *Physical Review Letters* 99:058302-1-058302-4 (2007).
Reisner et al. "Single-molecule denaturation mapping of DNA in nanofluidic channels" *Proc. Natl. Acad. Sci.* 107(30):13294-13299 (2010).
Reisner et al. "DNA confinement in nanochannels: physics and biological applications" *Rep. Prog. Phys.* 75(10):106601 (35 pages) (2012).
Riehn et al., "Restriction mapping in nanofluidic devices", *Proc. Natl. Acad. Sci.*, Jul. 19, 2005; vol. 102, No. 29, pp. 10012-10016.
Salieb-Beugelaar et al., "Electrophoretic separation of DNA in gels and nanostructures", *Lab Chip*, 2009, vol. 9, pp. 2508-2523.
Salieb-Beugelaar et al., "Field-Dependent DNA Mobility in 20 nm High Nanoslits", *Nano Letters*, Jul. 2008, vol. 8, No. 7, pp. 1785-1790.
Schoch, R.B. "Transport phenomena in nanofluidics" *Reviews of Modern Physics*, vol. 80, No. 3, Jul.-Sep. 2008, pp. 839-883.
Sebat et al., "Strong association of de novo copy number mutations with autism", *Science*, 2007, vol. 316, pp. 445-449.
Smeets et al. "Salt Dependence of Ion Transport and DNA Translocation through Solid State Nanopores" *Nano Letters* 2006, vol. 6, No. 1, 89.
Smith et al., "Overstretching B-DNA: The elastic response of individual double-stranded and single-stranded DNA molecules", *Science*, 1996, vol. 271, pp. 795-799.
So et al. "Inherently aligned microfluidic electrodes composed of liquid metal", *Lab Chip*, 2011, 11, 905-911.
Sorek et al., "Genome-wide experimental determination of barriers to horizontal gene transfer", *Science*, 2007, vol. 318, pp. 1449-1452.
Speicher et al., "Effect of genome-wide association studies, direct-to-consumer genetic testing, and high-speed sequencing technologies on predictive genetic counselling for cancer risk", *Lancet Oncol.*, Sep. 2010, vol. 11, pp. 890-898.
Stavis et al., "Nanofluidic structures with complex three-dimensional surfaces", *Nanotechnology*, 2009, vol. 20, Issue 16,165302, 7 pages.
Stefansson et al., "Large recurrent microdeletions associated with schizophrenia", *Nature*, 2008, vol. 455, pp. 232-236.
Striemer et al., "Charge- and size-based separation of macromolecules using ultrathin silicon membranes", *Nature*, Feb. 15, 2007; vol. 445, pp. 749-753.
Strychalski et al. "Diffusion of DNA in Nanoslits" *Macromolecules* 41:7716-7721 (2008).
Strychalski et al. "Non-planar nanofluidic devices for single molecule analysis fabricated using nanoglassblowing" *Nanotechnology* 19(16):315301 (2008).
Taniguchi et al., Fabrication of the gating nanopore device, *Applied Physics Letters*, 2009, vol. 95, pp. 123701-1-123701-3.
Teague et al., "High-resolution human genome structure by single-molecule analysis", *Proc. Natl. Acad. Sci.*, 2010, vol. 107, pp. 10848-10853.
Tegenfeldt et al., "The dynamics of genomic-length DNA molecules in 100-nm Channels", *Proc. Natl. Acad. Sci.*, Jul. 27, 2004; vol. 101, No. 30, pp. 10979-10983.
Tong et al., "Silicon Nitride Nanosieve Membrane", *Nano Letters*, 2004, vol. 4, No. 2, pp. 283-287.
Topolancik et al., "Extraction and purification of genomic DNA via entrapment in an array of microposts", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, p. 1026-1028.
Treangen et al., "Repetitive DNA and next-generation sequencing: computational challenges and solutions", *Nat. Rev. Genet.*, 2011, vol. 13, pp. 36-46.
Tseng, A. "Recent developments in micromilling using focused ion beam technology" *J. Micromech. Microeng.*, 2004, vol. 14, pp. R15-R34.
Tsutsui et al. "Transverse Field Effects on DNA-Sized Particle Dynamics" *Nano Letters* 2009, vol. 9, No. 4, 1659.
Turner et al., "Confinement-induced entropic recoil of single DNA molecules in a nanofluidic structure", *Phys. Rev. Lett.*, 2002, vol. 88, 128103.
Utko et al., "Injection molded nanofluidic chips: Fabrication method and functional tests using single-molecule DNA experiments", *Lab Chip*, 2011, vol. 11, pp. 303-308.
Viero et al., Hydrodynamic Manipulation of DNA in Nanopost Arrays: Unhooking Dynamics and Size Separation, small, 2011, pp. 3508-3518, vol. 7, No. 24.
Volkmuth et al., "Dna electrophoresis in microlithographic arrays", *Nature*, Aug. 13, 1992; vol. 358, pp. 600-602.
Wang et al. "Single-molecule studies of repressor-DNA interactions show long-range interactions" *PNAS* 102(28):9796-9801 (2005).
Wang et al. "Manipulating DNA molecules in nanofluidic channels" *Microfluid Nanofluid*, 2:85-88 (2006).
Wanunu, Meni "Nanopores: A journey towards Dna sequencing" *Physics of Life Reviews* 9:125-158 (2012).
Xu et al., "Wide-spectrum, ultrasensitive fluidic sensors with amplification from both fluidic circuits and metal oxide semiconductor field effect transistors", *Applied Physics Letters*, 2007, vol. 91, pp. 013901-1-013901-3.

(56) References Cited

OTHER PUBLICATIONS

Yuan et al., "Electrokinetic transport and separations in fluidic nanochannels", *Electrophoresis*, 2007, vol. 28, pp. 595-610.

Zangle et al., "Theory and experiments of concentration polarization and ion focusing at microchannel and nanochannel interfaces", Chem. Soc. Rev., 2010, vol. 39, pp. 1014-1035.

Zhou et al., "A single molecule system for whole genome analysis", *Perspectives in Bioanalysis, vol. 2, New High Throughput Technologies for DNA Sequencing and Genomics*; Mitchelson, K. R., Ed.; 2007, Elsevier: Amsterdam; pp. 265-300.

Zhou et al., "A whole-genome shotgun optical map of Yersinia pestis strain KIM", *Appl. Environ. Microbiol.*, 2002, vol. 68, No. 12, pp. 6321-6331.

Zhou et al., "Whole-genome shotgun optical mapping of Rhodobacter sphaeroides strain 2.4.1 and its use for whole-genome shotgun sequence assembly", *Genome Res.*, 2003, vol. 13, pp. 2142-2151.

Zhou et al., Transport and Sensing in Nanofluidic Devices, Annu. Rev. Anal. Chem., 2011, pp. 321-341, vol. 4.

Zhu et al. "Arrays of horizontally-oriented mini-reservoirs generate steady microfluidic flows for continuous perfusion cell culture and gradient generation" *The Analyst* 129:1026-1031 (2004).

Zwolak, M., "Electronic Signature of DNA Nucleotides via Transverse Transport", *Nano Letters*, 2005, vol. 5, No. 3, pp. 421-424.

\* cited by examiner

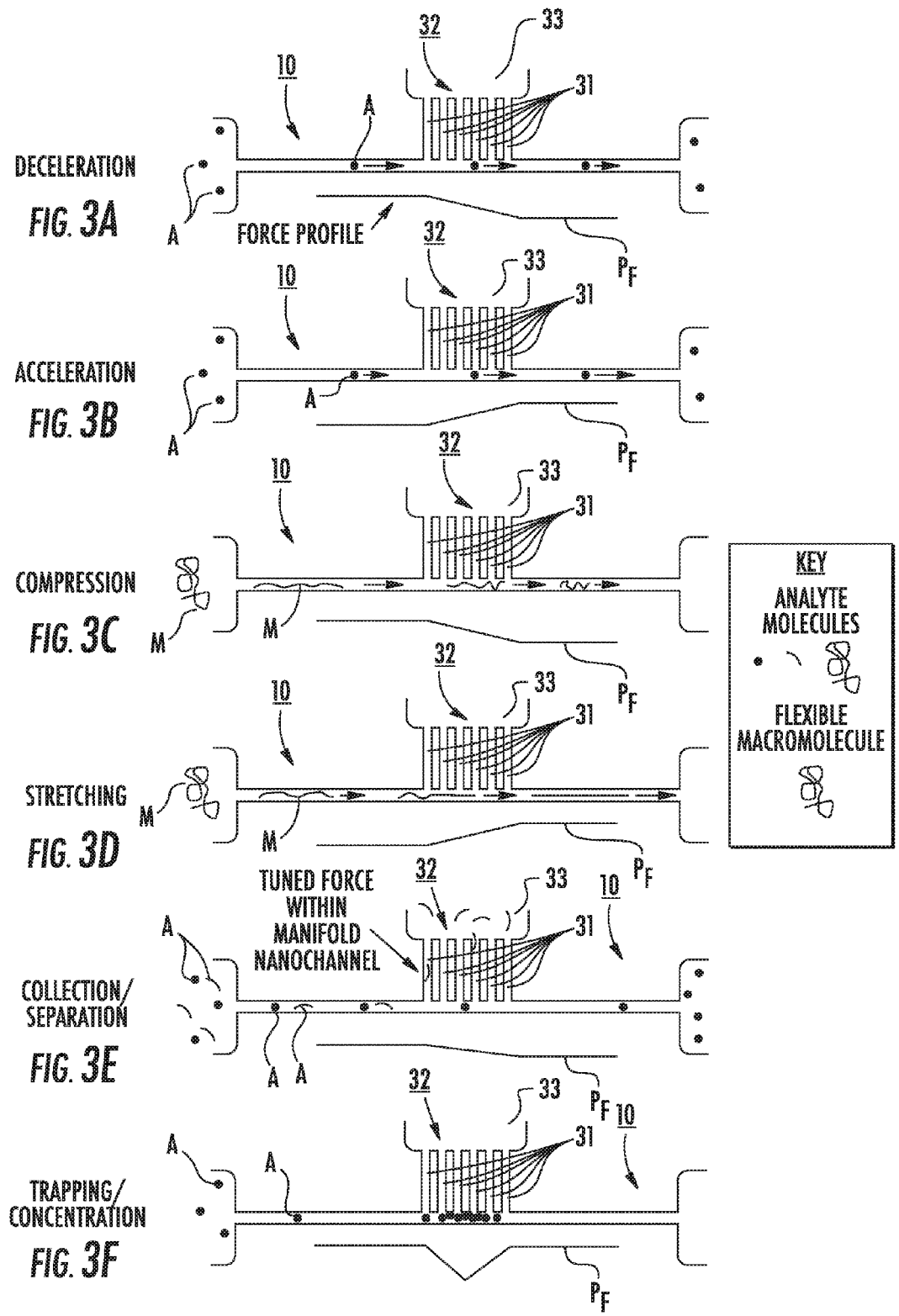

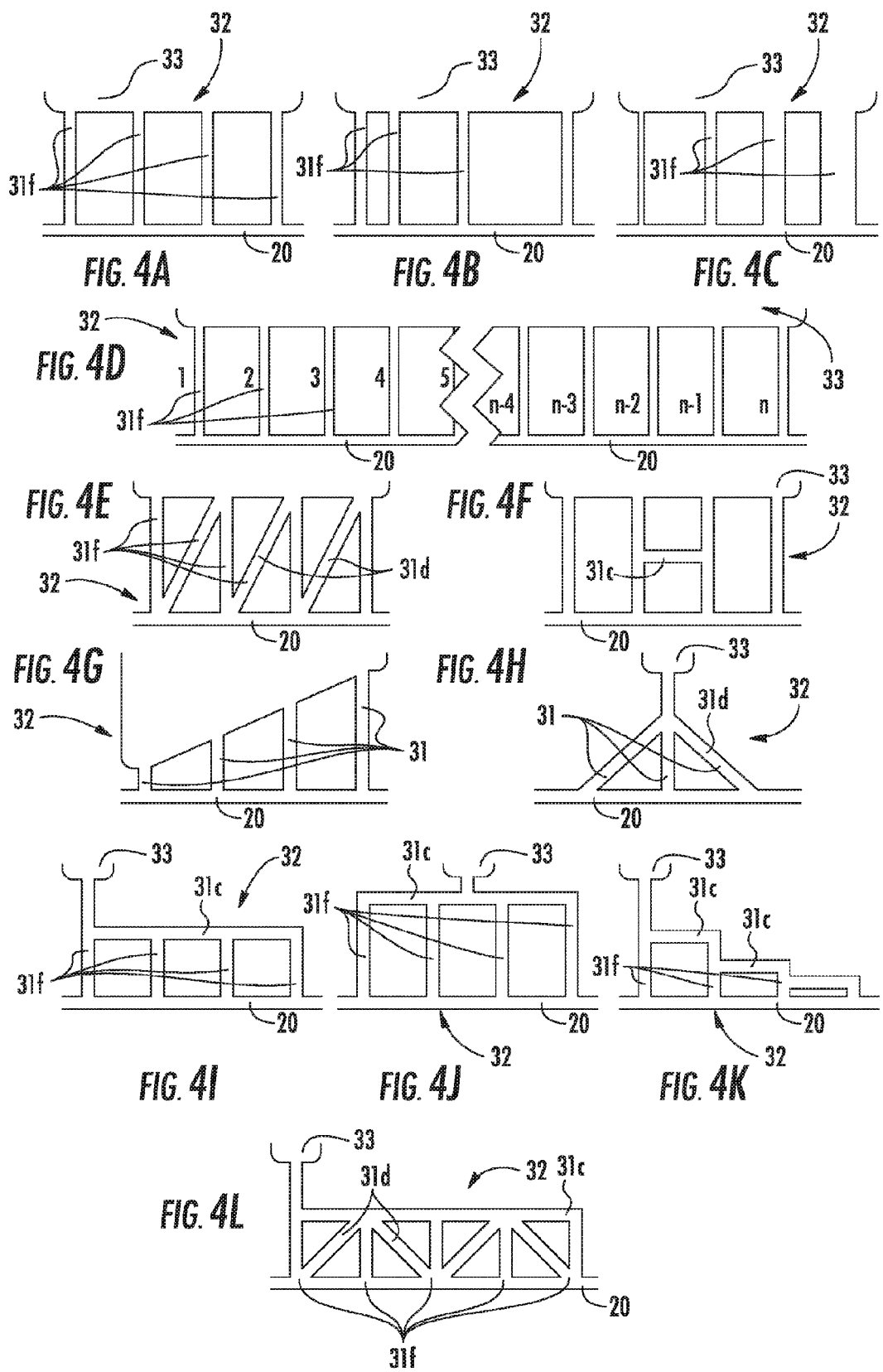

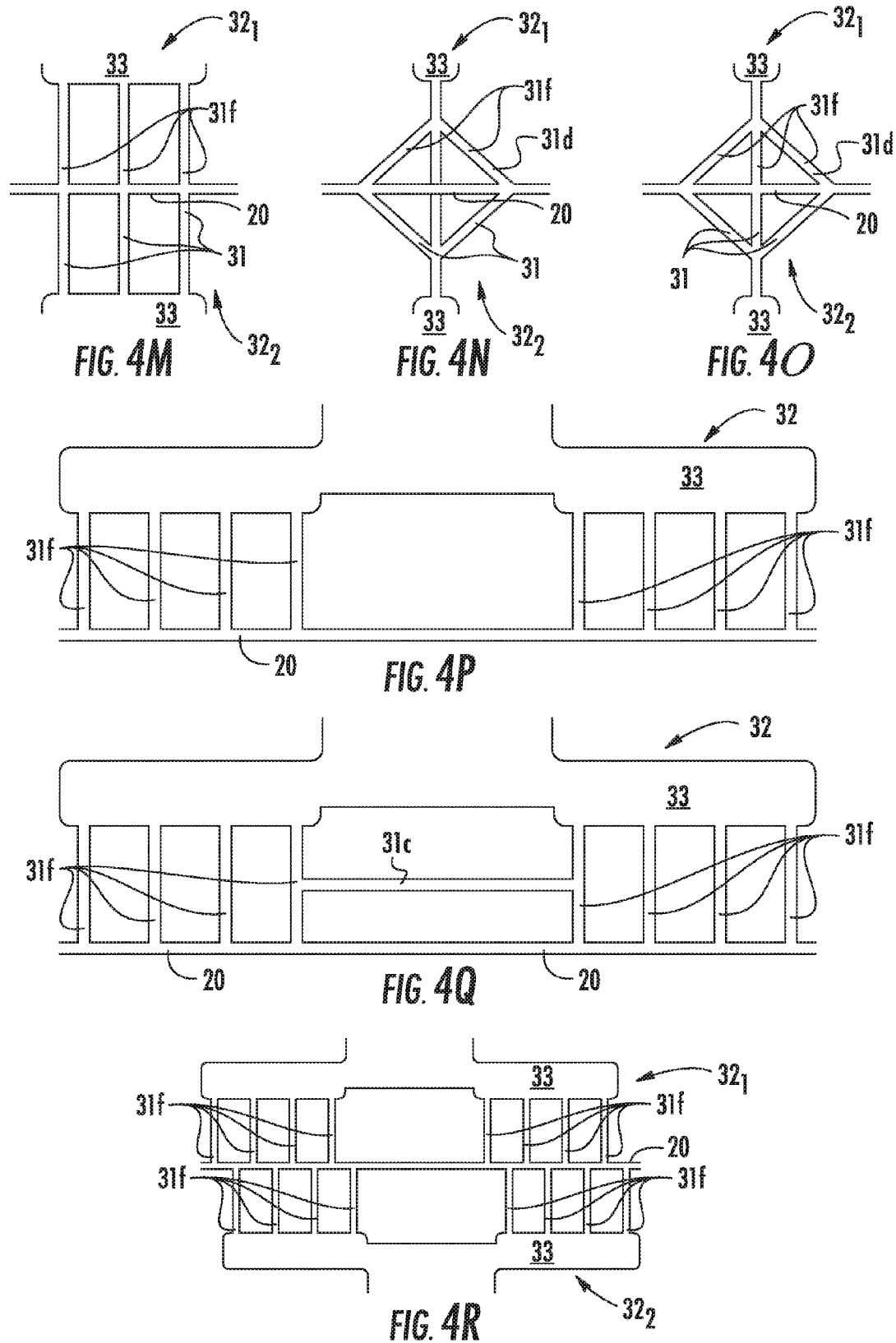

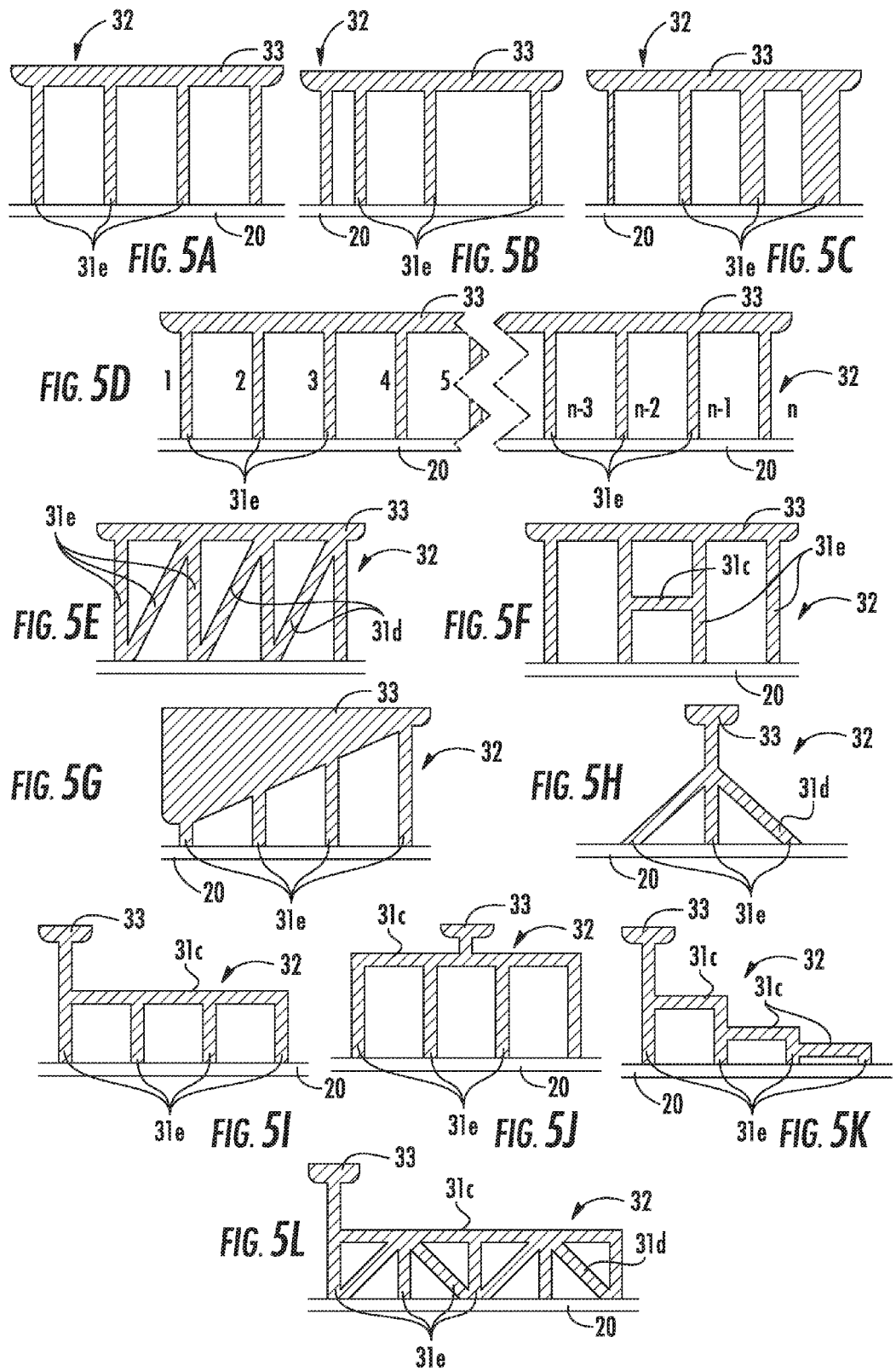

FLUIDIC DEVICES WITH NANOSCALE MANIFOLDS FOR MOLECULAR TRANSPORT, RELATED SYSTEMS AND METHODS OF ANALYSIS

RELATED APPLICATIONS

This application claims the benefit of and priority to U.S. Provisional Patent Application Ser. No. 62/159,503, filed May 11, 2015, the contents of which are hereby incorporated by reference as if recited in full herein.

STATEMENT OF FEDERAL SUPPORT

This invention was made with government support under Grant No. 1R01HG007407-01 awarded by the National Institutes of Health. The government has certain rights in the invention.

FIELD OF THE INVENTION

This invention relates to "lab on a chip" fluidic devices and may be particularly suitable for molecular transport along a fluidic nanochannel for analyzing various target analytes in samples.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences include, for example, double-layer overlap (DLO) and its effect on electro-osmosis and charge perm-selectivity, localized enhancement of electric fields, higher surface to volume ratios, confinement effects on large synthetic and bio-polymers, and the emerging importance of entropic effects. See, e.g., Yuan et al., *Electrophoresis* 2007, 28, 595-610; Schoch et al., *Rev. Mod. Phys.* 2008, 80, 839-883; and Kovarik et al., *Anal. Chem.* 2009, 81, 7133-7140. Historic examples of nanoscale devices include the use of porous media and gels in chromatographic separations and filtration membranes with nanoscale pores. See, e.g., Lerman et al., *Biopolymers* 1982, 21, 995-997; and Tong et al., M. *Nano Lett.* 2004, 4, 283-287. Recent efforts, however, have been focused on engineering geometrically well-defined conduits for fluid and analyte transport and seamlessly integrating them into devices. See, e.g., Volkmuth et al., *Nature* 1992, 358, 600-602; and Striemer et al., *Nature* 2007, 445, 749-753. The advantage of such regular structures is the relative simplicity of pressure and field gradients, fluid flow, and molecular motion contained within, in contrast to these properties in more tortuous networks. The capability to define, characterize, and easily model these systems can allow a better understanding of separation mechanisms and single molecule physics, for example. See, e.g., Volkmuth et al., *Nature* 1992, 358, 600-602; Reisner et al., *Phys. Rev. Lett.* 2005, 94, 196101; and Salieb-Beugelaar et al., *Lab Chip* 2009, 9, 2508-2523.

Recently FIB milling techniques have been described to form nanofluidic devices. See, Menard et al., Fabrication of Sub-5 nm Nanochannels in Insulating Substrates Using Focused Ion Beam Milling, Nano Lett. 2011, 11, 512-517 (published Dec. 20, 2010); and U.S. Provisional Patent Application Ser. No. 61/384,738, filed Sep. 21, 2010 (and related PCT Application PCT/US2011/052127), entitled, Methods, Systems And Devices For Forming Nanochannels, the contents of which are hereby incorporated by reference as if recited in full herein. In addition to FIB milling, a variety of other methods suitable for nanochannel fabrication can be used, including, for example, electron beam lithography, nanoimprint lithography, photolithography, templating or molding strategies, and other methods understood by one of ordinary skill in the art.

A number of nanofluidic devices have been proposed, including those with integrated miniature electrodes (nano- or micro-scale) for single-molecule sensing and/or nucleic acid sequencing. However there remains a need for alternative designs.

SUMMARY OF EMBODIMENTS OF THE INVENTION

Embodiments of the invention provide fluidic devices with one or more nanoscale manifolds for incorporation within fluidic lab-on-a-chip devices that are designed for the active control of the capture, manipulation, and transport of analyte molecules. The nanoscale manifolds, e.g., arrays or networks of nanochannels, nanoslits, or nanoelectrodes, are joined to a common voltage and/or pressure source, and are interfaced to at least one primary transport nanochannel. Each bank of nanoscale manifolds can be configured to allow precise and active control over the forces driving molecular transport in the various regions of the primary nanochannel(s). This allows for control over the transport of molecules along discrete regions of the primary nanochannel(s). The manifold structures can permit the establishment of designed monotonic force gradients along the length of the primary fluidic nanochannel(s) while limiting the required number of independent input potentials or pressures applied to the device. These tunable force gradients can be used for the manipulation of small molecules and macromolecules spanning many orders of magnitude in size while minimizing the occurrence of force gradient induced molecular fragmentation. Through the decoupling of the force magnitudes required to capture and then transport molecules through a nanochannel, precise spatio-temporal control over the molecules can be obtained.

Some embodiments are directed to fluidic devices that include at least one fluidic transport nanochannel; and at least one nanoscale manifold having a plurality of nanoscale elements. At least a plurality of the nanoscale elements directly interface with the at least one fluidic transport nanochannel. At least a plurality of the nanoscale elements of the nanoscale manifold are configured to be concurrently controlled by a common externally applied pressure and/or voltage to generate a force gradient within the at least one transport nanochannel.

The fluidic device can be a chip.

The device can further include a plurality of reservoirs including at least one reservoir in fluid communication with at least one microfluidic inlet to at least one transport nanochannel and at least one reservoir in fluid communication with a plurality of the nanoscale elements of the at least one nanoscale manifold.

The at least one nanoscale manifold can include at least first and second nanoscale manifolds interfaced to a first one of the at least one transport nanochannel.

The first nanoscale manifold can be upstream of the second nanoscale manifold.

The first nanoscale manifold can face the second nanoscale manifold across the first fluidic transport nanochannel.

The plurality of nanoscale manifold elements can be between 2-10,000 adjacent elements that directly interface with at least one transport nanochannel. At least some of the adjacent elements can be spaced apart by 10 nm to 1 cm.

The plurality of nanoscale manifold elements for a respective transport nanochannel can be one of: (a) between 2-10, (b) between 10-100, (c) between 100-1000, or (d) between 1000-10,000.

The nanoscale manifold elements can include nanoslits.

The nanoscale manifold elements can include nanoelectrode elements.

The nanoscale manifold elements can include nanochannels.

The nanoscale manifold can include at least one cross-channel that connects at least two parallel nanoscale manifold elements that directly interface with at least one of the at least one transport nanochannels.

The nanoscale manifold elements can include at least one diagonal element.

The at least one diagonal manifold element can extend outward from at least one straight manifold element.

The at least one diagonal element can extend from a voltage and/or pressure input junction or channel segment associated therewith to the at least one transport nanochannel.

The at least one fluidic transport nanochannel can be a plurality of discrete, spaced apart fluidic transport nanochannels. The at least one nanoscale manifold can interface with at least two of the plurality of transport nanochannels.

The at least one nanoscale manifold can interface with first and second spaced apart segments of at least one of the at least one fluidic transport nanochannel.

The at least one transport nanochannel may have a serpentine shape with first and second legs that may be parallel. At least one of the at least one nanoscale manifold can interface with both the first and second legs.

The device can be in combination with power and/or pressurized gas supplies and at least one controller in communication with the power and/or pressurized gas supplies.

Each nanoscale manifold can be controlled by a separate voltage and/or pressure input and are addressed individually.

A single pressure and/or voltage input to a respective nanoscale manifold can feed only its respective manifold elements.

Each primary transport nanochannel can have voltage and/or pressure inputs that are separate from a respective nanoscale manifold inputs.

Other embodiments are directed to analysis systems. The systems include: (a) a fluidic analysis device comprising: at least one fluidic transport nanochannel; at least one nanoscale manifold having an array of nanoscale elements, at least some of the nanoscale elements interface directly with the at least one fluidic transport nanochannel; (b) a first power and/or first pressurized gas supply in communication with a single one of the at least one nanoscale manifolds to feed voltage and/or pressure to its respective nanoscale elements so that the nanoscale manifold applies a force gradient on an analyte in the transport nanochannel; and (c) at least one additional pressurized gas supply and/or power supply in communication with the transport nanochannel proximate an entrance and exit end portion thereof. Voltages and/or pressures at the entrance and exit of the transport nanochannel and at each respective nanoscale manifold can be independently controlled.

The at least one nanoscale manifold can optionally include first and second spaced apart nanoscale manifolds that both interface with at least one of the at least one fluidic transport nanochannels.

Each nanoscale manifold can have an independent pressurized gas supply and/or voltage input whereby each nanoscale manifold is independently addressable.

Still other embodiments are directed to methods of controlling the transport of molecules within a fluid for the purposes of analysis. The methods can include providing a fluidic analysis device, the analysis device having at least one primary transport nanochannel and at least one nanoscale manifold with a plurality of nanoscale elements that intersect or interface with at least one primary transport channel; and automatically concurrently applying a single pressure and/or single voltage input to multiple nanoscale elements of a respective nanoscale manifold to generate a force profile on the at least one transport nanochannel to carry out at least one of: accelerate, decelerate, compress, stretch, collect/separate or trap/concentrate an analyte as the analyte flows through the at least one primary transport nanochannel proximate the nanoscale manifold.

The at least one nanoscale manifold can be a plurality of nanoscale manifolds, each interfacing with at least one of the at least one transport nanochannel. Each nanoscale manifold can be independently controlled to apply a force gradient to a respective transport nanochannel.

The nanoscale manifold elements can include fluidic nanoscale elements.

The nanoscale elements can include nanoelectrodes.

The method can further include controlling molecular transport in the at least one transport nanochannel by selectively dynamically changing force gradients applied by the nanoscale magnitude.

The controlling can be carried out by changing the force gradient in one or more of magnitude, shape, and polarity using a single external voltage input and/or a single pressure input to each of the plurality of nanoscale manifolds.

The controlling can include varying a single external voltage input and/or a single pressure input to each of a plurality of nanoscale manifolds in a time-dependent manner such as stepping to different voltages or pressures, transiently pulsing to different voltages or pressures, continuously ramping at various linear or non-linear rates, or varying according to a sinusoidal or other wave function.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 3A-3F are schematic illustrations of a fluidic analysis device with exemplary different actions using a nanoscale manifold to generate a defined force profile for a respective action according to embodiments of the present invention.

DESCRIPTION OF EMBODIMENTS OF THE INVENTION

Figure 1A:
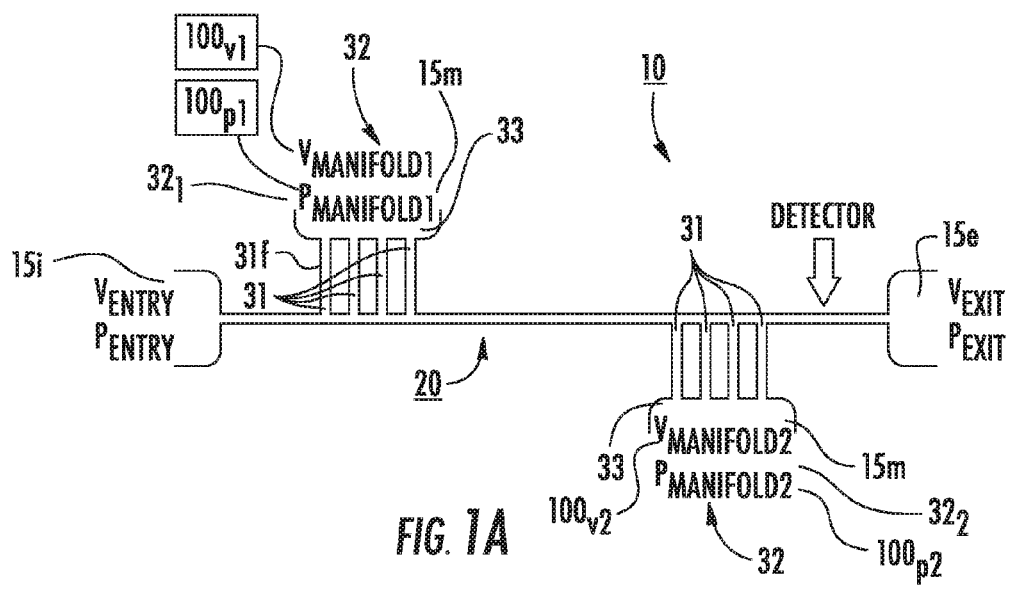
FIGS. 1A and 1B are schematic illustrations of a fluidic analysis device according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity.

The terminology used herein is for the purpose of describing particular embodiments only and is not intended to be limiting of the invention. As used herein, the singular form, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "nanochannel" refers to a channel or trench having a critical dimension that is on the order of nanometers. The nanochannel has sidewalls and a floor. The nanochannel can be formed into a solid substrate to have an open top surface and a closed bottom surface with the sidewalls extending therebetween. A cover may be used to seal or otherwise close the upper surface of the nanochannel(s). The term "primary dimension" (also known as the "critical dimension") refers to a width and/or depth dimension. The primary dimension of a transport nanochannel can be between about 1 nm to about 900 nm, and is more typically between about 10 nm to about 500 nm. Different nanochannels on any particular substrate can have different primary dimensions and can change in magnitude over its length.

The term "about" refers to parameters that can vary between +/−20% or less, such as +/−10%.

The terms "transport nanochannel" and "primary transport nanochannel" and "fluidic transport nanochannel" are used interchangeably herein and refer to a nanochannel through which an analyte flows for manipulation and/or analysis.

The analyte can be any analyte of interest including, for example, single analyte molecules including synthetic and biological macromolecules, nanoparticles, small molecules, DNA, nucleic acids/polynucleic acids, peptides, proteins and the like. The transport through the nanochannel can be carried out using electrokinetics, concentration polarization and/or hydraulic pressure (forced pressure or pressure gradients) with at least one nanoscale manifold.

The term "nanoscale manifold" refers to an array or network of nanoscale elements that include one or more of nanochannels, nanoslits or nanoelectrodes. The nanoscale manifolds can be comprised of a single type of nanoscale element or combinations of two or more of these three types of nanoscale elements. At least some, and in some embodiments, all, the nanoscale elements of a respective nanoscale manifold are joined to a common voltage and/or pressure source and interfaced to one or more primary transport nanochannels, e.g., a single primary transport nanochannel, a plurality of primary transport nanochannels, or an array of primary transport nanochannels. The nanoscale manifold can have nanoscale elements that directly interface with a respective transport nanochannel or nanoscale elements that indirectly interface with a respective transport nanochannel by way of nanoscale elements that directly interface with the transport nanochannel as will be discussed below. The nanoscale manifold can have a plurality of nodes. The term "node" refers to a point at which nanoscale elements, e.g., nanoelectrodes, nanoslits or nanochannels, intersect or branch between a voltage and/or pressure source and a respective primary transport nanochannel.

The term "nanoslit" refers to channels that have nanometer scale depths but micrometer or larger widths. Nanoslits can have a depth between about 1 nm to about 900 nm, and more typically between about 10 nm to about 500 nm and the depth and/or width can be constant or vary over a length of the nanoslit. Nanoslits have typical depth:width aspect ratios between about $1 \times 10^{-8}$ to about 0.2, more typically between about $1 \times 10^{-5}$ to about 0.01.

The term "nanoelectrode" refers to a structure having a critical dimension that is on the order of nanometers consisting of an electrically conductive solid and/or non-flowable material including, for example, metals, metal carbides, carbon, semiconductors, conductive polymers, and gels. The critical dimension (or primary dimension) refers to a width and/or depth dimension. The primary dimension of a nanoelectrode can be between about 1 nm to about 900 nm, and is more typically between about 10 nm to about 500 nm. Different nanoelectrodes on any particular substrate can have different primary dimensions and can change in magnitude over its length.

The term "upstream" indicates a relative position that is closer to the ingress end of the primary transport nanochannel. The term "downstream" indicates a relative position that is closer to the egress end of the primary transport nanochannel.

The term "circuit," when referring to a control system for the fluidic chip, refers to an entirely hardware embodiment or an embodiment combining software and hardware using one or more controller.

The term "size", when referring to a sample, means that fragments are pulled into a segment of the transport channel (which can be identified as a detection nanochannel at that location), creating separation from neighbors for the determination of the size of fragments by detecting electrical or optical signal duration or amplitude.

The term "chromosomal DNA" means an entire chromosome's complement of DNA or a fragment of same.

Embodiments of the invention are directed to genomic mapping of DNA in a nanofluidic device but other uses are contemplated.

Analytes of interest that can be evaluated using a fluidic device with at least one nanoscale manifold include small molecules, nucleic acids, proteins, peptides, polysaccharides, viruses, ribosomes, micelles, and nanoparticles, for example.

The fluidic devices contemplated by embodiments of the invention can be configured to be able to characterize and/or controllably transport nucleic acids to various reservoirs associated with the fluidic devices with at least one nanoscale manifold, which may be useful for pooling genomic elements for assembly into synthetic genomes.

Systems using one or more of the fluidic devices contemplated by embodiments of the invention can include one or more detectors for detecting signals of onboard analytes. The detected signal may be analyzed to determine, for example, the identity of an analyte, structural conformation, size, positions of targeted or functional sites, or sequence of component units (e.g., nucleotides in polynucleic acids, amino acids in proteins, prosthetic groups, and blocks in block co-polymers).

Figure 1B:
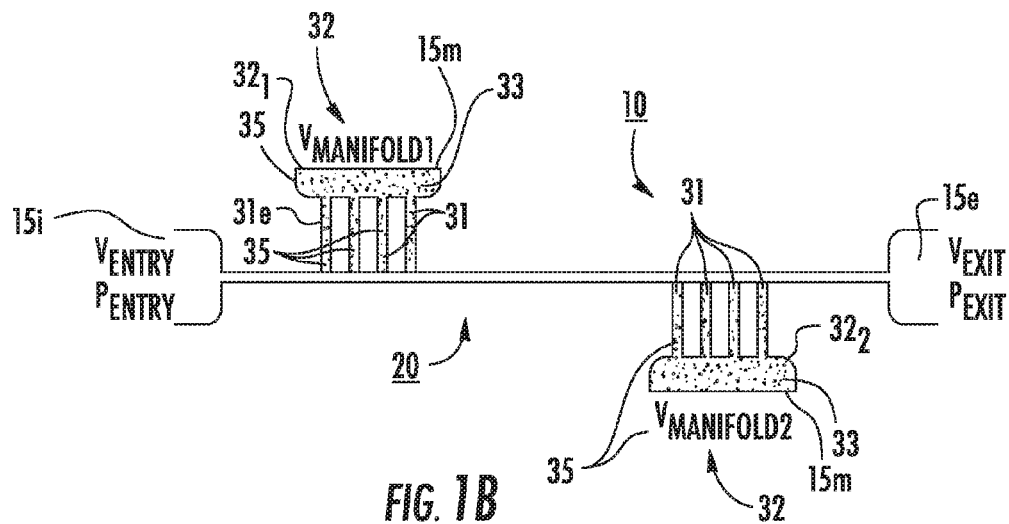

FIGS. 1A and 1B illustrate exemplary fluidic analysis devices 10. FIGS. 1A and 1B illustrate the fluidic analysis devices 10 can have at least one nanoscale manifold 32 that interfaces with (e.g., are in electrical and/or fluid communication with) at least one primary transport nanochannel 20.

The primary transport nanochannel 20 can be linear or curvilinear and may have a width and/or depth that changes at the entrance and/or exit or at other segments along lengths thereof. For example, the transport nanochannel 20 can have a reaction channel segment that is deeper and/or wider than a detection channel segment.

As shown in FIGS. 1A and 1B, there are first and second spaced apart manifolds $32_1$, $32_2$, each with a plurality of nanoscale elements 31 which can form pathways with nodes. As shown in these examples, the nanoscale elements 31 can each directly interface with the primary transport channel 20. At least a plurality of nanoscale elements 31 of each respective manifold 32 extend from a common (single) voltage or pressure source junction 33, typically a microchannel 15m, to interface with at least one primary transport channel 20. Thus, a nanoscale manifold 32 comprises a common voltage and/or pressure junction 33 for a plurality of nanoscale elements 31. The voltage and/or pressure junction 33 can be attached to a manifold reservoir $50_2$ (FIG. 13) or other input connector for external input to supply pressure P ($100p_2$, FIG. 13) and/or voltage V ($100v_2$, FIG. 13) concurrently to a plurality of nanoscale elements 31 of a respective nanoscale manifold 32. In the embodiment shown in FIGS. 1A and 1B, the manifold 32 has a pressure/voltage junction 33 that concurrently supplies voltage and/or pressure to all nodes 31n of a respective nanoscale manifold 32.

Although each manifold 32 in FIGS. 1A and 1B is shown with four nanoscale elements 31 with four nodes 31n, more or fewer directly interfacing nanoscale elements 31 with more or fewer nodes 31n may be used. Where more than one manifold 32 is used, each can have the same or different numbers of nanoscale elements 31, but at least two nanoscale elements 31 that directly interface with the primary nanochannel 20 at a corresponding number of spaced apart locations.

FIG. 1A illustrates the nanoscale elements 31 can be fluidic nanoscale elements 31f such as nanochannels or nanoslits with voltage V and/or pressure P at the microchannel 15m for supplying the input to the nodes 31. In some embodiments, the fluidic nanoscale elements 31 can have a shallow channel depth, which, in some embodiments, can prevent DNA molecules from entering the respective manifold nanochannel due to an energy barrier because of the additional confinement. This allows a relatively high field in the manifold element, e.g., nanochannel, which is desirable for significantly slowing down (or speeding up) the molecular transport. However, the fluidic nanoscale element 31f may also have a deep but narrow channel for similar function.

FIG. 1B illustrates a device 10 similar to FIG. 1A but with nanoelectrodes 31e as the nanoscale elements 31 that can include a non-flowable conductive medium or material 35 (shown by the darker background in the elements 31). Nanoelectrodes 31e as the manifold elements 31 can be constructed from a variety of non-flowable materials including, for example, metals, metal carbides, carbon, semiconductors, conductive polymers, and gels. Such electrodes 31e can be patterned using lift-off lithography, electron beam induced deposition, ion beam induced deposition, lithography and subtractive etching, dielectrophoretic or direct manipulation of nanoelectrodes, templated growth of electrodes within nanochannels or nanoslits, injection of melted or suspended conductive or semiconductive media into nanochannels or nanoslits, in situ polymerization or gelation within nanochannels or nanoslits, and other methods known to those of skill in the art.

Each manifold 32 can be individually addressable by a common or an independent voltage and/or pressure source $100v_1$, $100v_2$ and/or $100p_1$, $100p_2$, as shown schematically in FIG. 1A. Thus, the nanoscale manifold 32 can allow multiple control elements 31, e.g., nodes 31n, to be addressed from the same voltage and/or pressure input. The multiple interfaces/intersections of the nanoscale elements 31 to the primary nanochannel(s) 20 can result in a series of nodes 31n with separate characteristic voltages or pressures, as shown schematically in an equivalent circuit diagram in FIG. 1C.

The voltage and/or pressure differences between nanoscale elements 31 can drive the electrokinetic or pressure driven flow, respectively, of analyte molecules in the nanochannel 20. FIGS. 1A and 1B show an exemplary fluidic device 10 with two nanoscale manifolds $32_1$, $32_2$ interfaced to a single transport nanochannel 20. It should be understood that any number of nanoscale manifolds 32 can be interfaced to a single and/or a plurality of primary transport nanochannels 20 as will be discussed below.

A respective manifold 15m can have any suitable number of manifold elements 31, such as between 2-10, between 10-100, between 100-1000, between 1000-10,000 (or even more depending on the application).

FIG. 1A is an example of a fluidic device 10 where the forces driving transport are controlled by the application of voltages (V) and/or pressures (P) at the microchannels 15m accessing the primary nanochannel entrance 15i, its exit 15e, and the nanoscale manifold elements 31. In FIG. 1A, the nanoscale manifold elements 31 are nanoslits or nanochannels. In FIG. 1B, the device 10 has nanoscale manifold elements 31 that have a non-flowable, electrically conductive medium (indicated in shading/darker background). Here, transport control can be carried out by applying voltages V to at least the manifold inputs 15m. Voltages and/or pressures can be applied at the primary nanochannel entrance and exit 15i, 15e, respectively, to affect molecular transport.

Figure 1C:
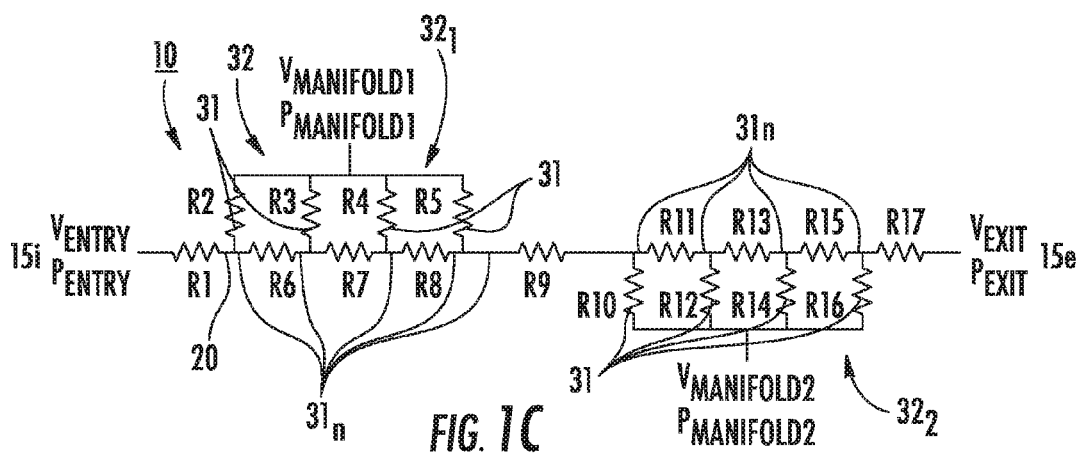
FIG. 1C is an equivalent circuit diagram of the fluidic devices shown in FIGS. 1A and 1B according to embodiments of the present invention.

FIG. 1C is an equivalent circuit showing how the applied voltages and/or pressures V, P can be divided across the various manifold nodes 31n and/or nanoscale elements 31 and different segments of the primarily transport nanochannel 20. Resistance to the electrical current is equal to the resistivity ($\rho$) of the medium in the segment multiplied by the segment's length (L) and divided by its cross sectional area (A); $R_{electrical} = \rho L/A$. Resistance to hydrodynamic flow depends on the geometry of the fluidic nanoscale element. An example is for channels with circular cross-sections with radius a: $R_{hydrodynamic}$, circular-channel cross-section: $L/a^4$. Another example is for channels with rectangular cross-sections having width w and depth h: $R_{hydrodynamic}$, rectangular channel cross-section: $L/(wh^3 (1-0.63 h/w))$.

Generally stated, each nanoscale manifold 32 can be controlled by a separate voltage and/or separate pressure source. Additionally, the primary transport nanochannel(s) 20 at an entrance portion 15i and exit portion 15e can each be addressed by its own pressure and/or voltage source(s). Thus, each manifold 32 can be modular. That is, each manifold 32 can be addressed individually, a single pressure or single voltage control (or a combination single voltage and pressure control) affects many elements 31 in a given manifold 32. Device 10 performance can be engineered by fabricating/assembling multiple manifolds 32 that are interfaced to the primary transport nanochannel 20 or a plurality of primary transport nanochannels 20. For example 2, 3, 4, 5, 6, 7, 8, 9, 10, 10s, 100s, 1000s, or more nanoscale manifolds 32 can be interfaced to the primary transport nanochannel 20 or a plurality of primary transport nanochannels 20.

The spacing of the nanoscale manifold elements 31, their dimensions, their connectivity, and their conductivity can be designed to control their resistances (electrical or hydraulic) and shape the force profiles within the primary transport nanochannel(s) 20 and within nanoscale elements 31.

The spacing between adjacent nanoscale elements 31 and/or nodes 31n of a respective manifold 32 can vary or be the same. The spacing between adjacent nanoscale elements 31 can be nm size spacing, (100s of) μm size spacing and, even mm size spacing. Typically, the spacing between adjacent nanoscale elements 31 and/or nodes 31n is between about 10 nm to about 20 μm, more typically between 0.5 μm and 10 μm such as 0.5 μm, 0.6 μm, 0.7 μm, 0.8 μm, 0.9 μm, 1 μm, 2 μm, 3 μm, 4 μm, 5 μm, 6 μm, 7 μm, 8 μm, 9 μm and 10 μm. In other embodiments, the spacing between adjacent nodes 31 for a respective manifold 32 can be between 100 nm and 6000 nm, such as 100 nm, 115 nm, 120 nm, 125 nm, 130 nm, 135 nm, 140 nm, 145 nm, 150 nm, 155 nm, 160 nm, 165 nm, 170 nm, 175 nm, 180 nm, 190 nm, 195 nm, 200 nm, 210 nm, 220 nm, 230 nm, 240 nm, 250 nm, 260 nm, 270 nm, 280 nm, 290 nm, 300 nm, 310 nm, 320 nm, 330 nm, 340 nm, 350 nm, 360 nm, 370 nm, 380 nm, 390 nm, 400 nm, 500 nm, 600 nm, 700 nm, 800 nm, 900 nm, 1000 nm, 1100 nm, 1200 nm, 1300 nm, 1400 nm, 1500 nm, 2000 nm, 2250 nm, 2500 nm, 3000 nm, about 3500 nm, about 4000 nm, about 4500 nm, about 5000 nm, about 5500 nm, and about 6000 nm and any increment therebetween, whether explicitly listed or not.

The device 10 can have a body that is a planar chip with a pattern of microchannels 15i, 15e and 15m (the manifold microchannel 15m can merge into nanoscale elements 31) that communicate with the at least one nanochannel 20 as shown in FIGS. 1A and 1B. The device 10 can include a cover that can be attached (typically bonded) to a substrate with the pattern of channels. In some embodiments, some features, e.g., one or more of the micro and/or nanochannels 15i, 15e, 20 and/or one or more of the manifolds 15m and/or nanoscale manifold elements 31 can be patterned on the substrate while others can be patterned on the cover plate. Reservoirs $50_1$, $50_2$, $50_3$ may be mounted on the device 10 at various microchannel interfaces, 15i, 15m, 15e (FIG. 13), for example.

The transport nanochannel 20 can be deeper and more narrow (in width) than the depth and/or width of all or some of the nanoscale elements 31 of a respective nanoscale manifold 32.

In some embodiments, the nanoscale elements 31 can be shallow. The term "shallow" refers to manifold nanochannel elements 31 with depths that are less than a depth of an associated transport nanochannel 20 and can be smaller than analyte macromolecules' hydrodynamic sizes. With respect to the depth, a shallow manifold nanochannel or nanoslit 31 can have a depth that is typically less by at least a factor of two (2), such as by between 2-100× less than that of an associated transport channel 20.

The at least one manifold 32 can be configured to produce a defined monotonic gradient in the electric field (FIG. 2A) or pressure (FIG. 2B), which may be particularly important for some uses/analysis. The field strength "E" V/cm or velocity "U" μm/s of an analyte with a mobility $1 \times 10^{-4}$ cm$^2$/(V·s) is illustrated by the vertical graduated scale to the right of FIG. 2A. The linear flow rate "F" μm/s for the pressure-driven flow is shown in FIG. 2B with the appended scale to the right of the figure.

Figure 2A:
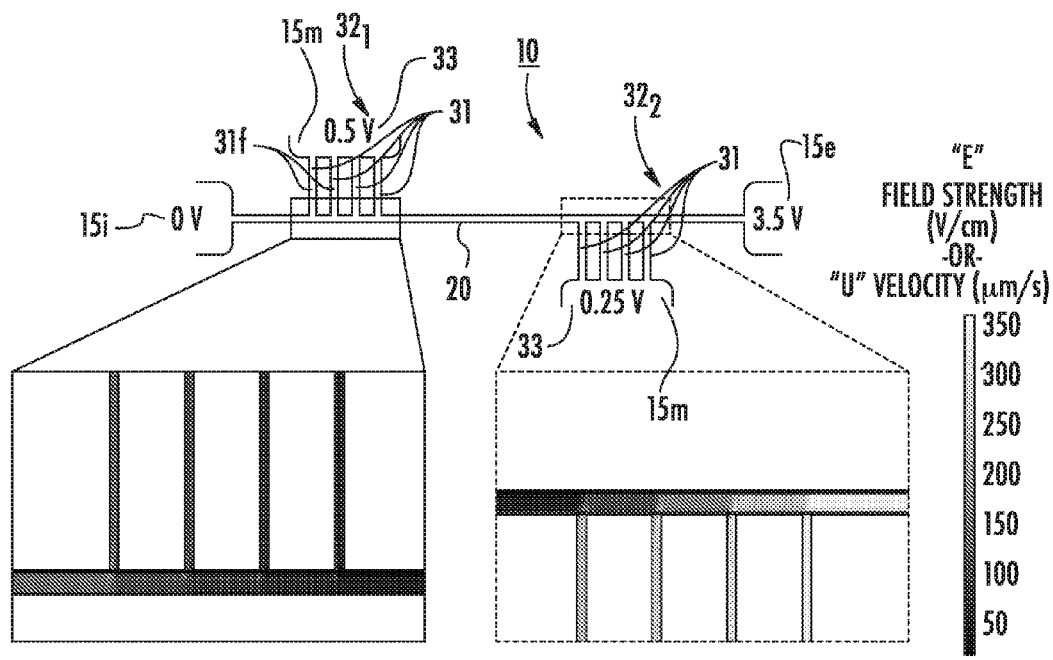
FIG. 2A is an enlarged view of a portion of a fluid device with dual nanoscale manifolds with associated greatly enlarged insets with a grayscale of intensity representing field strength (V/cm) or velocity (μm/s) of an analyte with exemplary voltage controlled operation according to embodiments of the present invention.
Figure 2B:
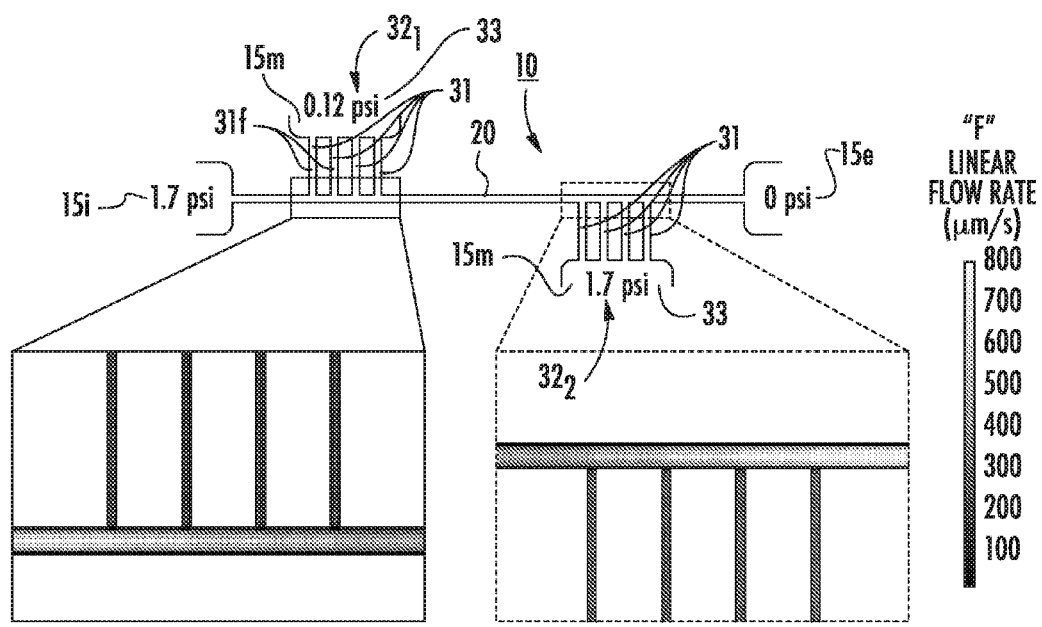
FIG. 2B is an enlarged view of a portion of a fluid device with dual nanoscale manifolds with associated greatly enlarged insets with a grayscale of intensity representing linear flow rate (μm/s) with exemplary pressure controlled operation according to embodiments of the present invention.

FIGS. 2A and 2B provide examples of operation of a fluidic device 10 where the manifold elements 31 are nanoslits or nanochannels. The drawings are not to scale. In this example, the primary nanochannel 20 is 320 nm wide×

440 nm deep with a total length of 275 µm. In this example, each of the nanoscale manifold elements 31 is 550 nm wide×65 nm deep×18 µm long. The spacing between (node) nanochannel elements 31 within a manifold 32 is 5 µm for this example. FIG. 2A illustrates exemplary voltages for the manifolds $32_1$, $32_2$ for a voltage controlled operation. The electric field strengths (and analyte velocity) in the vicinity of the manifolds $32_1$, $32_2$ are indicated in the enlarged insets by the grayscale intensity. These were calculated using the voltages provided in the schematic. FIG. 2B illustrates pressure-controlled operation of the manifold 32. The linear flow velocities in the vicinity of the manifolds are indicated by the grayscale intensity. These were calculated using the pressures provided in the schematic. All calculations were performed using finite element analysis implemented in COMSOL Multiphysics® modeling software, a general-purpose software platform, based on advanced numerical methods, for modeling and simulating physics-based problems from Comsol Inc., Burlington, Mass. and Los Angeles and Palo Alto, Calif.

Several examples of use of fluidic devices 10 with exemplary force profiles ("force profiles" is used interchangeably with "force gradients") $P_F$ that can be applied by a nanoscale manifold 32 to the transport nanochannel 20 are shown in FIGS. 3A-3F for analyte molecules A, represented by solid circles, arcuate lines and a longer curvilinear "flex" line (the latter for flexible macromolecule M). For example, by appropriately increasing or decreasing the electric field strength within a primary transport nanochannel 20, an analyte A such as a flexible macromolecule can be accelerated (FIG. 3B) or decelerated (FIG. 3A) without inducing shearing, i.e., covalent bond breakage. These features allow gentle handling of fragile molecules, reducing shear forces across a wide range of transport velocities within a primary nanochannel FIG. 3C illustrates compression, FIG. 3D illustrates stretching, FIG. 3E illustrates collection/separation and FIG. 3F illustrates trapping/concentration. The number and architecture of the nanoscale manifold elements can be tailored to the application. The simplicity of device design and fabrication may be the primary consideration when the anticipated analyte is mechanically robust. More complex manifolds 32 might be more suitable for the most fragile analytes, where a premium is placed on very gradually changing the transport driving forces.

Through the application of electric potentials and/or pressures to the entrance and exit of the primary nanochannel 15i, 15e and/or nanoscale manifold elements 31 and/or nodes 31n of the manifold 32, each nanoscale manifold 32 can establish an independent decelerating or accelerating force gradient within the primary transport nanochannel(s) 20 for a desired force profile $P_F$. By way of example, in operation, a manifold 32 placed close to the entry location 15i of an analyte into the transport channel 20 (e.g., left manifold $32_1$ in FIG. 1A) can decelerate analyte macromolecules A after they are initially forced into a transport nanochannel 20. This "close" spacing can be between 100 nm and 20 µm, for example. Given the entropic barrier to entry into a transport nanochannel 20 a relatively strong force may be required to thread macromolecules into the primary nanochannel 20. This force can inject molecules into the primary nanochannel 20 at high velocity, resulting in their elongation and exposure to significant shear forces. Use of the manifold 32 can significantly and gradually decrease the magnitude of the transport driving force within the primary nanochannel 20, minimizing the shear force on the macromolecules and decreasing their velocity within the transport nanochannel 20. Downstream of the first manifold $32_1$, such as at an exit end portion of the transport nanochannel 15e, a second manifold $32_2$ (FIGS. 1A, 1B) can be employed to accelerate the molecules out of the primary nanochannel 20, for example past an optical detector "Di" and/or electrical detector "De" (FIG. 1A, 13) for analysis. The applied forces can be held constant throughout a respective experiment or can be switched or otherwise varied during the experiment to alter the dynamics of molecule transport.

Generally stated, input voltages and/or pressures at the entrance and exit of the transport nanochannel 15i, 15e and at the nanoscale manifold(s) 15m can be independent of each other and controlled and output adjusted independently.

In some embodiments, the primary transport nanochannel 20 can have an aspect ratio ("AR")(depth:width) of ~1; typically the primary transport nanochannel 20 has an AR that is greater than 0.5 and less than 2. In some embodiments, the nanoscale elements 31 (nanoslits or nanochannels) can have aspect ratios less than unity and less than the transport channel 20. However, manifold nanochannels and nanoslits 31f can have a variety of aspect ratios.

When nanochannels or nanoslits are used as the nanoscale manifold elements 31, however, care should be taken to avoid unwanted molecular transport out of the primary transport nanochannel(s) 20 and into the manifold fluidic conduits 31f. This can be achieved by selecting the driving forces such that the forces that drive continued transport of a target analyte molecule through the primary nanochannel(s) 20 are greater than those driving transport down the manifold nanoscale fluidic elements 31f.

When the analytes of interest are large macromolecules, the use of manifold nanochannels or nanoslits 31f that have either widths or depths that are significantly (e.g., shallow depths) less than those of the primary transport nanochannel(s) 20 can also assist in ensuring that analytes remain in the primary nanochannel 20. This results from an entropic free energy barrier that inhibits macromolecule entry into a more constraining conduit. Correspondingly, manifold nanoscale fluidic elements 31f could also have the reciprocal AR to utilize entropic free energy barriers to keep macromolecules in the primary transport nanochannel(s) 20 but typically it is easier to fabricate low AR features than high AR features. Such considerations are not typically a concern when nanoscale electrodes are the manifold elements 31 used to generate transport-driving electric fields.

Figure 4S:
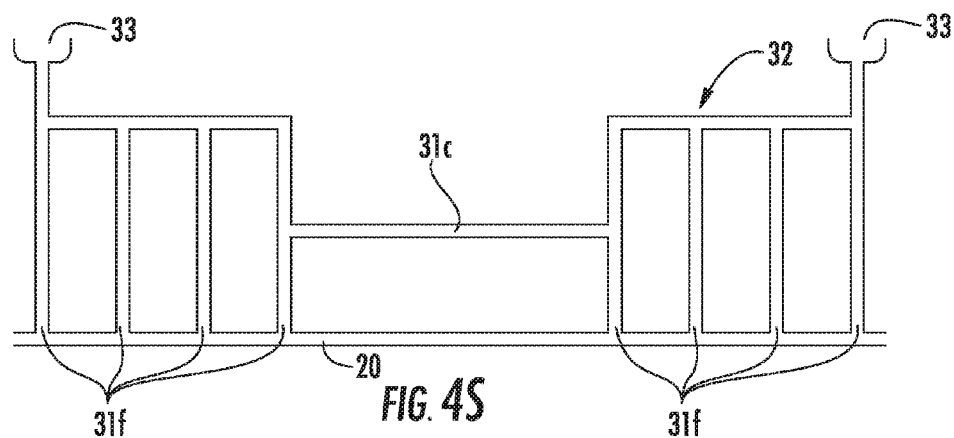
FIGS. 4A-4V are enlarged exemplary nanoscale manifold configurations with nanochannels and/or nanoslits according to embodiments of the present invention.
FIG. 4W is an enlarged illustration of an exemplary nanoscale manifold with nanochannels and/or nanoslits interfaced to an array of discrete, separate primary transport nanochannels according to embodiments of the present invention.
FIGS. 4X and 4Y illustrate exemplary nanoscale manifolds with nanochannels and/or nanoslits interfaced to multiple different segments of a common primary transport nanochannel according to embodiments of the present invention.
Figure 4T:
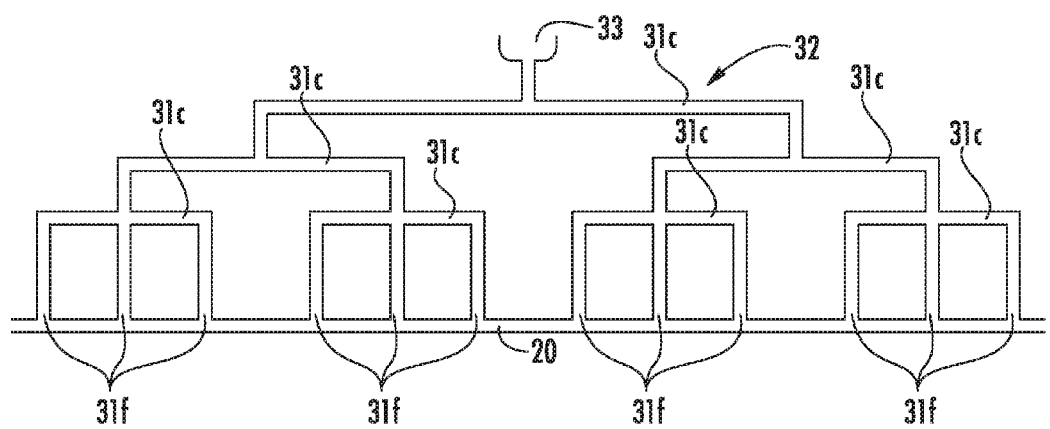
Figure 4U:
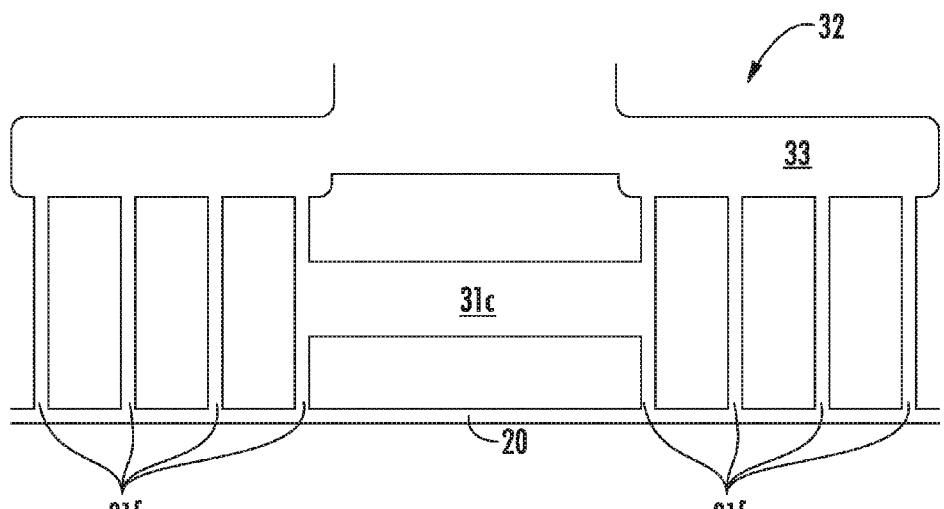
Figure 4V:
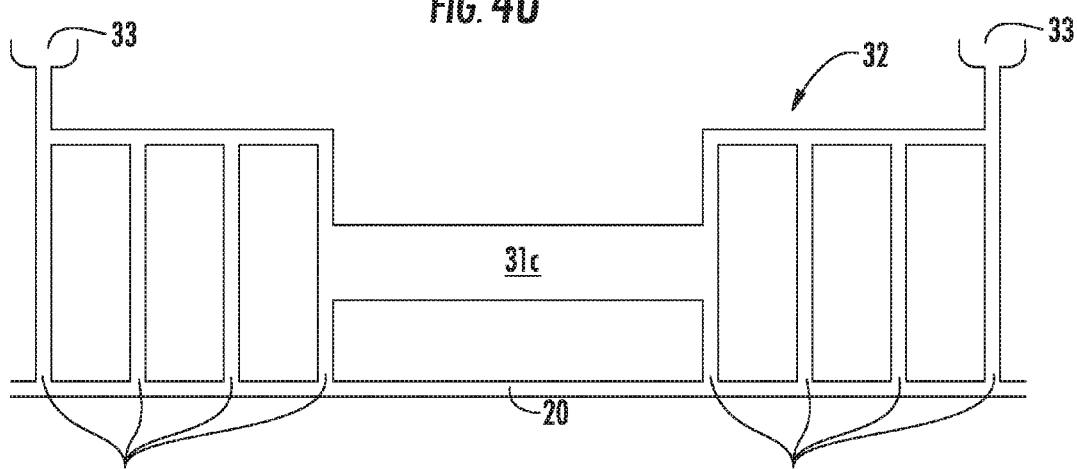
Figure 4Y:
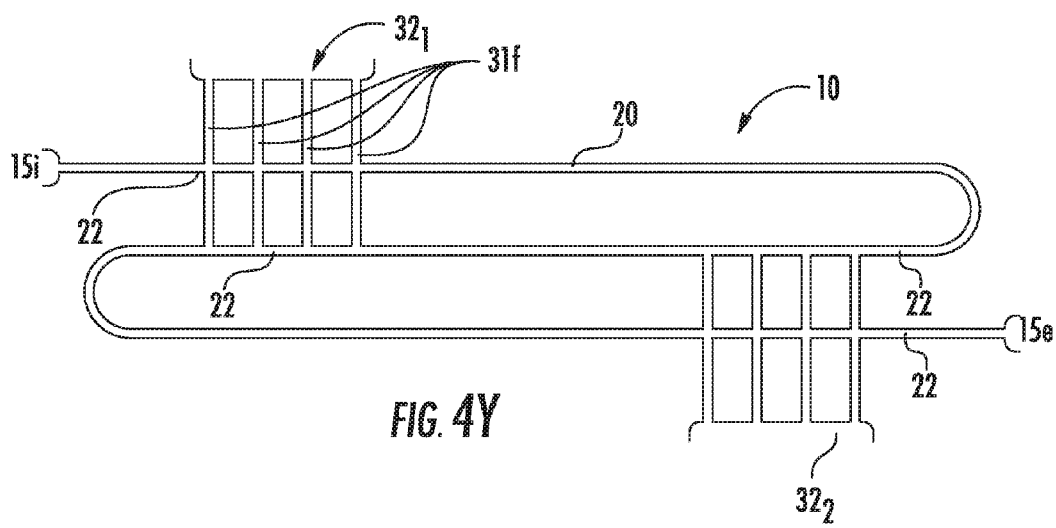
Figure 5M:
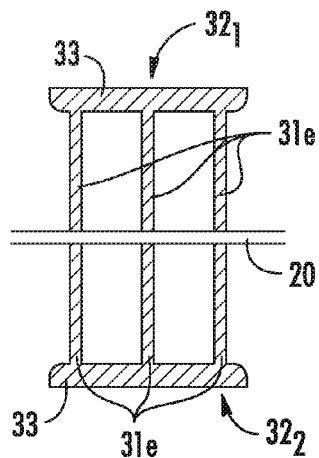
FIGS. 5A-5V are enlarged exemplary nanoscale manifold configurations with nanoelectrodes according to embodiments of the present invention.
FIG. 5W is an enlarged illustration of an exemplary nanoscale manifold with nanoelectrodes interfaced to an array of discrete, separate primary transport nanochannels according to embodiments of the present invention.
FIGS. 5X and 5Y illustrate exemplary nanoscale manifolds with nanoelectrodes interfaced to multiple different segments of a common primary transport nanochannel according to embodiments of the present invention.
Figure 5N:
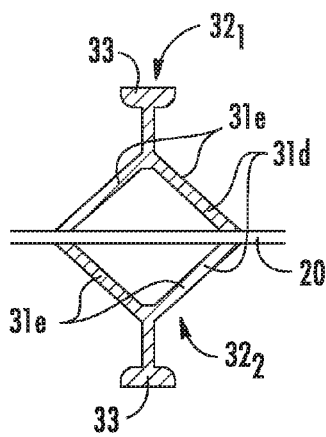
Figure 5O:
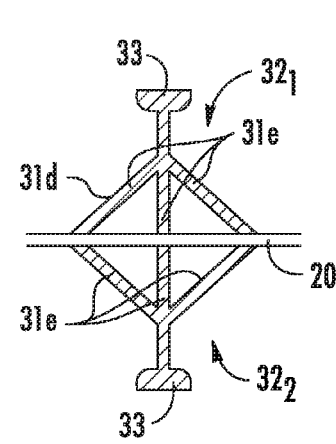
Figure 5P:
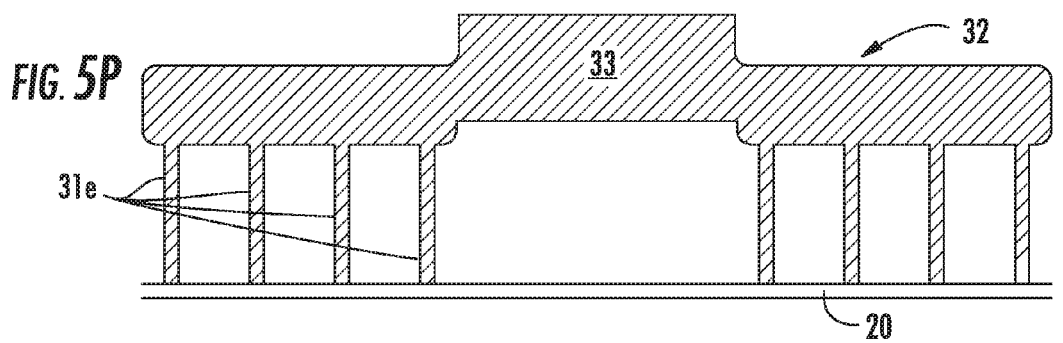
Figure 5Q:
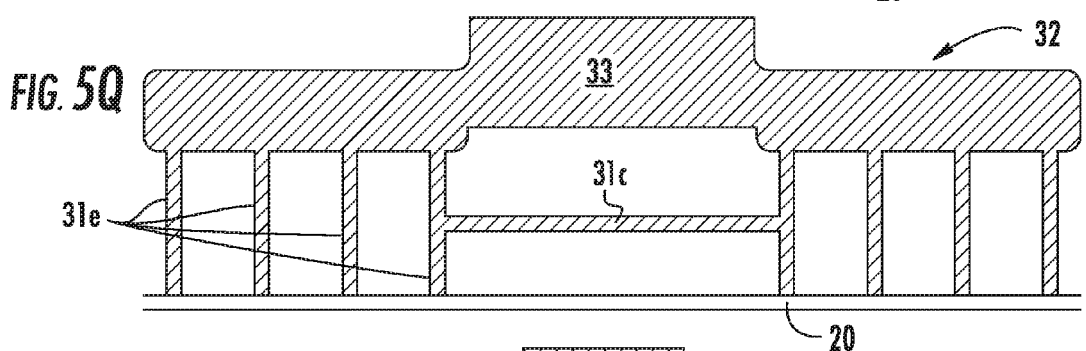
Figure 5R:
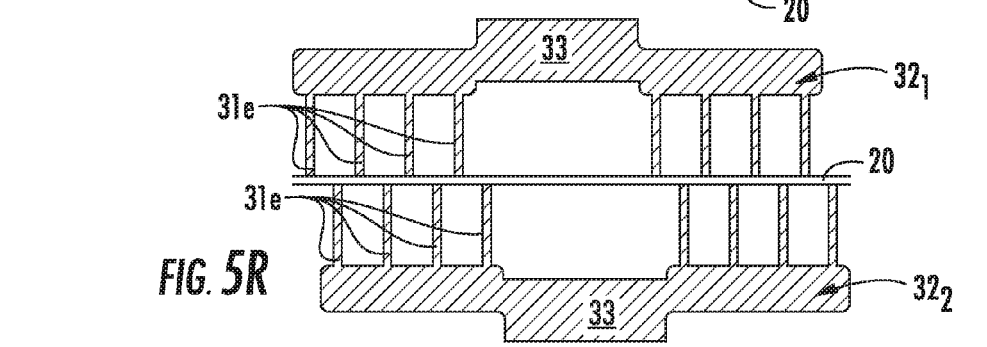
Figure 5S:
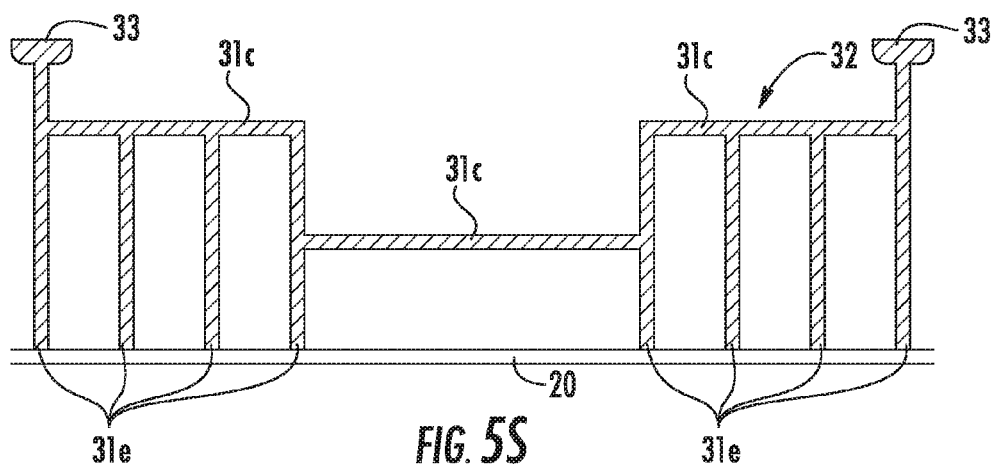
Figure 5T:
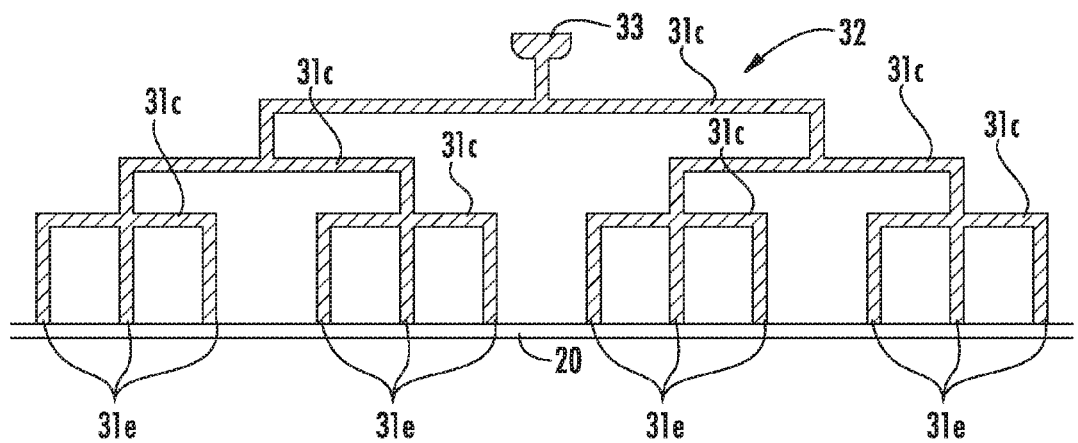
Figure 5U:
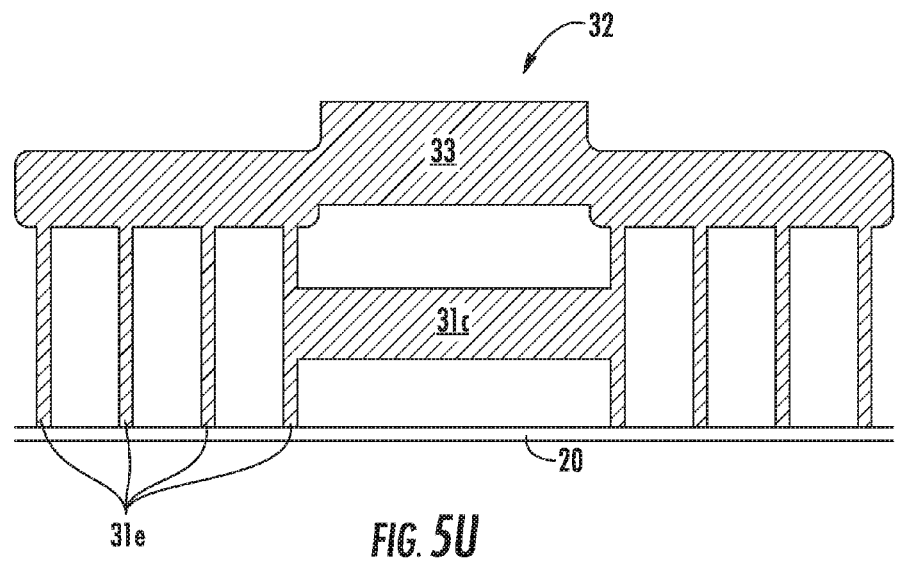
Figure 5V:
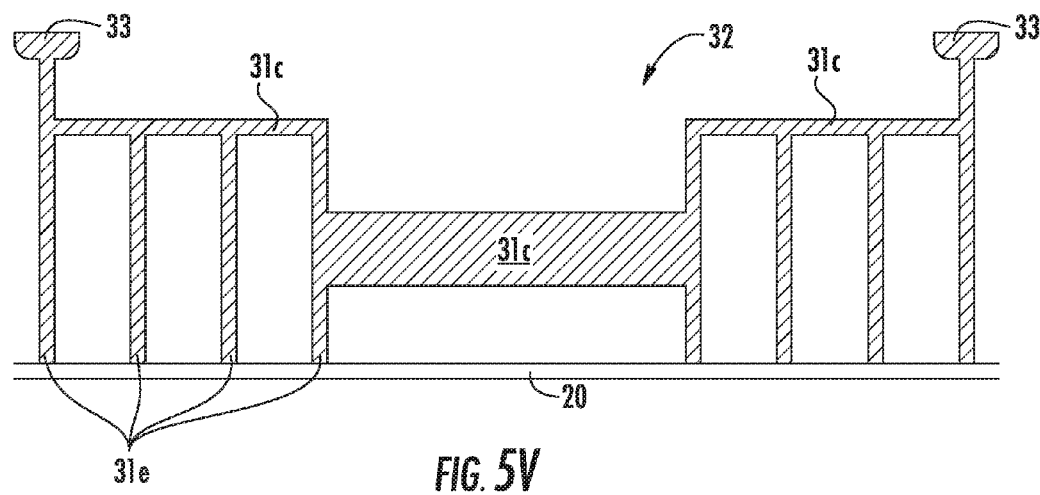

A variety of geometries for the nanoscale manifold elements 31 are possible, allowing the device 10 to be customized or tailored for specific sample and operational needs. FIGS. 4A-4Y show examples of manifold array geometries with nanofluidic elements 31f coupled to one pressure and/or voltage interface 33 or coupled to more than one spaced apart interface, with each interface communicating directly with at least two nanoscale manifold elements 31. FIGS. 5A-5Y illustrate corresponding manifold array geometries with nanoelectrodes 31e. FIGS. 4M, 5M, 4N, 5N, 4O, 5O, and 4R, 5R illustrate cooperating pairs of nanoscale manifolds $32_1$, $32_2$, positioned to face each other across the transport channel 20.

FIGS. 4E, 5E, 4H, 5H, 4L, 5L, 4N, 5N and 4O, 5O illustrate diagonal elements 31d, some that directly interface with the transport nanochannel 20 at a discrete node intersection (FIGS. 4H, 5H, 4N, 5N, 4O, 5O) and others that merge into another manifold element 31 to form a common, shared node (4E, 5E, 4L, 5L) at the intersection with the transport nanochannel 20.

FIGS. 4F, 5F, 4I, 5I, 4J, 5J, 4K, 5K, 4L, 5L, 4Q, 5Q, 4S, 5S, 4T, 5T, 4U, 5U and 4V, 5V, for example, illustrate at least one cross-channel 31c connecting different elements or forming a series of nodes (shown as perpendicular to the nanoscale elements 31). Some of the cross-channels 31c can indirectly interface with the transport nanochannel 20 via other nanoscale elements 31.

FIGS. 4L and 5L, for example, illustrate the manifold 32 can have both diagonal and cross elements 31d, 31c.

Figure 4W:
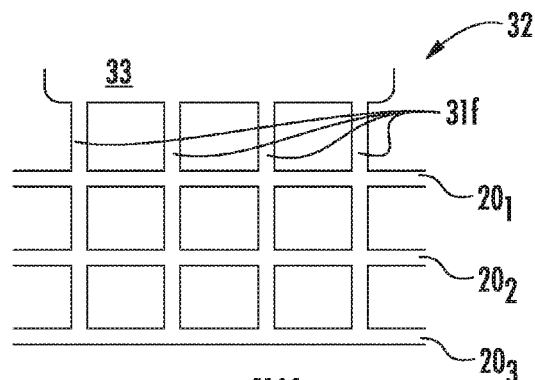
Figure 4X:
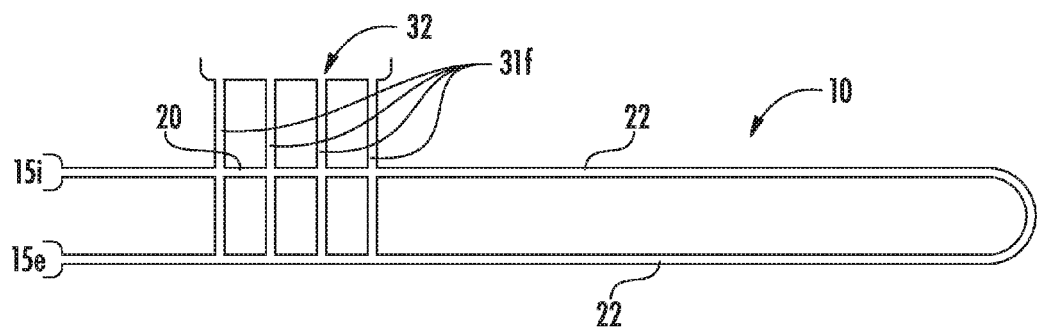
Figure 5W:
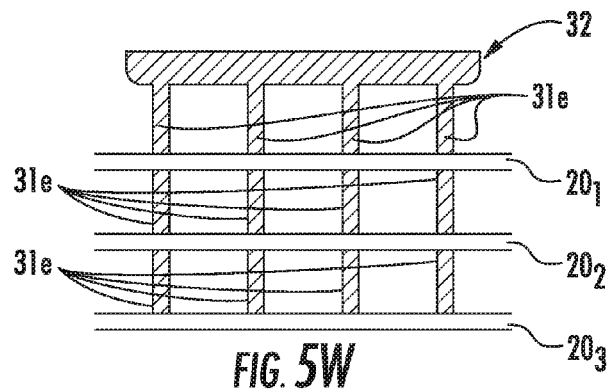
Figure 5X:
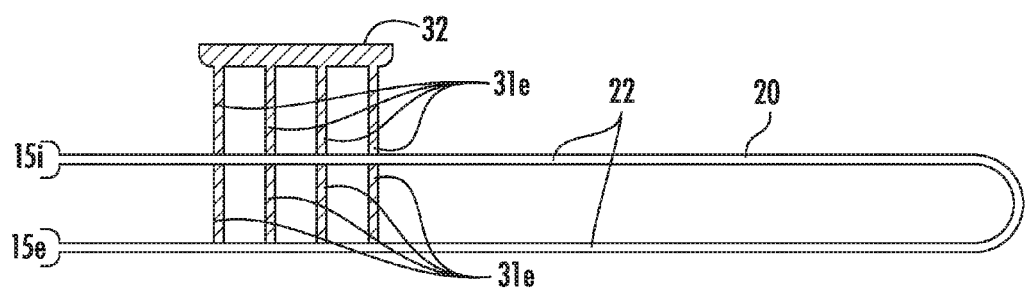
Figure 5Y:
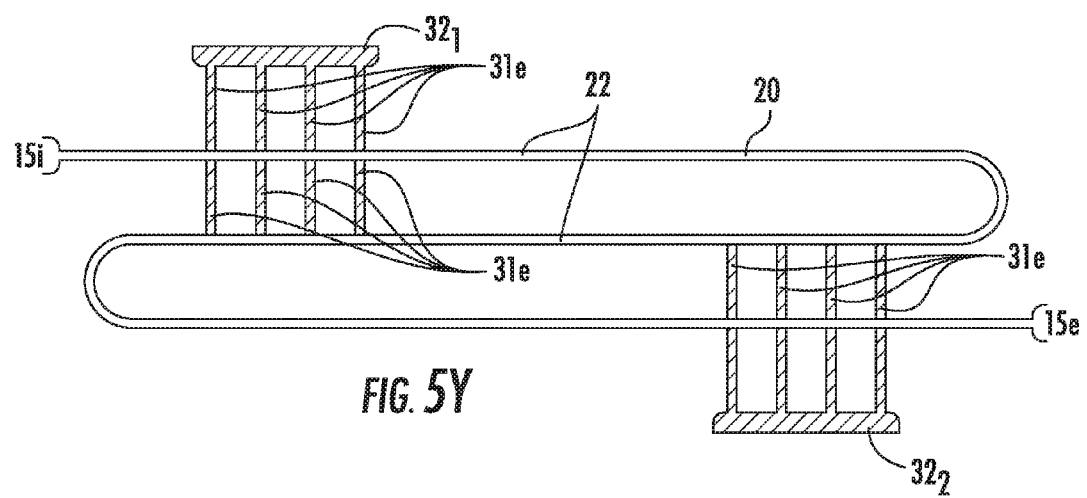
Figure 6A:
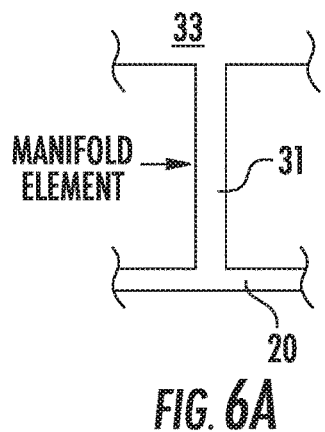
FIGS. 6A-6G illustrate exemplary geometries for nanoscale manifold elements according to embodiments of the present invention.
Figure 6B:
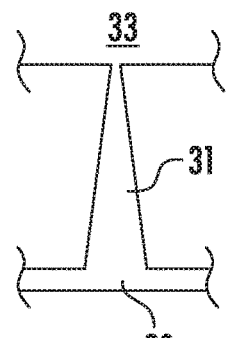
Figure 6C:
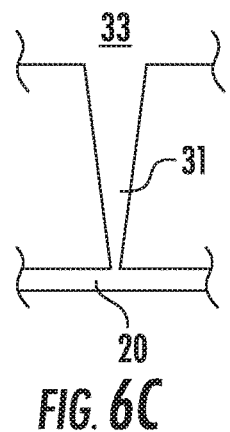
Figure 6D:
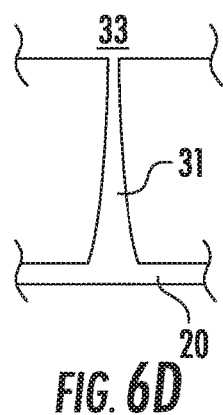
Figure 6E:
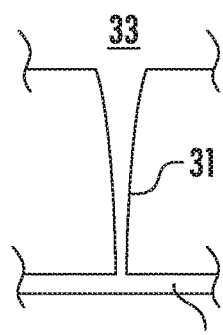
Figure 6F:
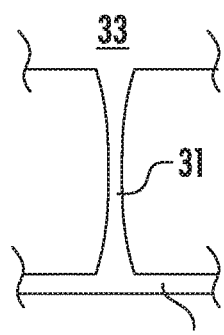
Figure 6G:
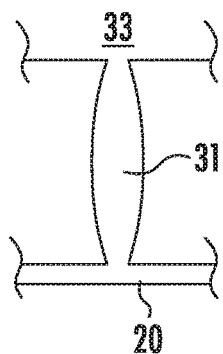

FIGS. 4W and 5W illustrates that the manifold 32 can be interfaced to a plurality of different transport nanochannels $20_1$, $20_2$, $20_3$ (e.g., an array of primary transport nanochannels).

FIGS. 4X, 5X and 4Y, 5Y illustrate the nanoscale manifold 32 can interface with a single transport nanochannel 20 at a plurality of spaced apart segments, typically where the transport channel 20 has a curvilinear or serpentine shape as shown so that the nanoscale elements 31 can interface with parallel legs 22 of the transport channel 20.

FIGS. 6A-6G show examples of nanoscale manifold elements 31 with various geometries that may be configured to provide additional control over manifold design. Such geometries can help shape the voltage or pressure gradients present in the primary transport nanochannel 20. In addition to width variations, the individual elements 31 can vary in their depth (for nanoslit or nanochannel manifold elements 31f) or thickness (for nanoelectrode manifold elements 31e). For example, the depth (thickness) of each element 31 can increase from the voltage or pressure source to the primary nanochannel 20, decrease from the voltage or pressure source to the primary nanochannel 20, decrease and then increase one or multiple times, or increase and then decrease one or multiple times. These variations in nanoscale element depth 31f or thickness 31e can occur in a step-wise fashion (e.g., a 100-nm change in feature depth over a length of 1 nm) or more gradually (e.g., a 100-nm change in feature depth over a length of 1 μm). A manifold 32 can consist of nanoscale elements 31 of identical geometries and dimensions or of nanoscale elements 31 having a variety of geometries and dimensions. Thus, FIGS. 6A-6G are greatly enlarged schematic top views of some of the many geometries that can be used for individual nanoscale manifold elements 31. In addition to variations in width shown, the depth of fluidic nanoscale elements 31f (for nanoslit and nanochannel manifold elements) or the thickness of nanoelectrode elements 31e can be varied along their lengths.

Figure 7A:
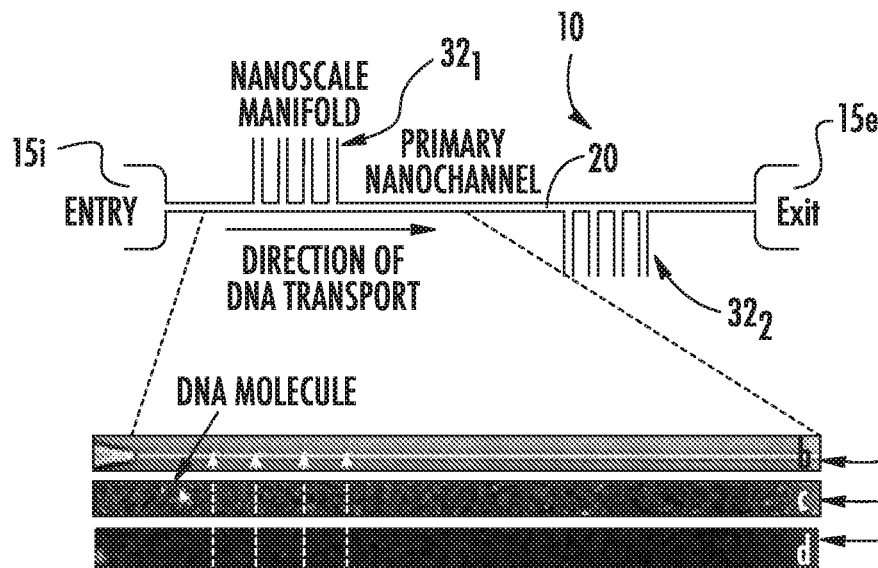
FIG. 7A is schematic illustration of a fluidic analysis device with a nanoscale manifold configured to decrease the velocity of molecular transport in a primary transport nanochannel (the arrow indicates the direction of molecular transport; in this example, the analyte is a molecule of DNA) according to embodiments of the present invention.
Figure 7B:
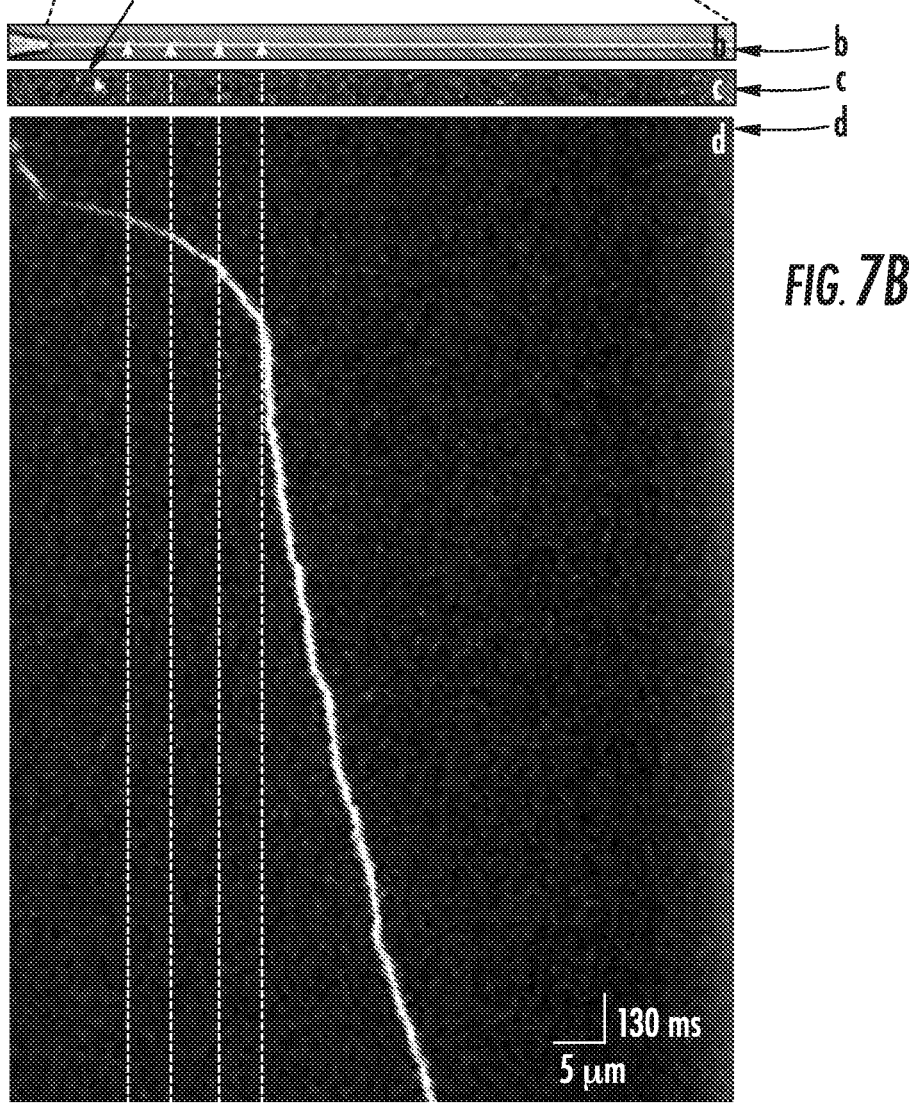
FIG. 7B shows adjacent images/panels (b), (c) and (d) of the transport nanochannel shown in FIG. 7A with a 10 kbp long DNA molecule stained with intercalating fluorescent dye according to embodiments of the present invention. Image (b) is a bright-field micrograph showing the entry region, the primary nanochannel and the manifold nanoslits Image (c) is a representative fluorescence image of a DNA molecule in the primary nanochannel. Image (d) is a kymogram (images recorded at 330 frames/second) showing the change in the DNA molecule's position over time as it is driven through the primary transport nanochannel. The position of the nanoslits in FIG. 7B are indicated by the vertical broken lines.

FIGS. 7A and 7B illustrate a fluidic device 10 with a nanoscale manifold 32 used to decrease the velocity of molecular transport within a primary nanochannel. In this example the analyte is a 10-kbp long DNA molecule stained with an intercalating fluorescent dye. FIG. 7A is a schematic of the device 10 used to collect the data shown in the images in FIG. 7B. Image (b) in FIG. 7B is a bright-field micrograph showing the entry region, primary nanochannel 20, and manifold nanoslits 31f. The field of view is restricted to the first ~80 μm of the primary nanochannel 20. Image (c) is a representative fluorescence image of a DNA molecule in the primary nanochannel 20. Image (d) is a kymogram (images recorded at 330 frames per second) showing the change in the DNA molecule's position over time as it is driven through the primary transport nanochannel. The positions of the manifold nanoslits are indicated by the dashed lines. The molecule is pulled into the primary nanochannel by a 186 V/cm magnitude electric field. The field strength in the primary channel is gradually lowered by the action of the nanoscale manifold to a magnitude of 32.7 V/cm to the right of the fourth manifold nanoslit. The total relative decrease in velocity is 5.68-fold. The 10-kbp DNA molecule (1 kbp=1,000 base pairs) underwent rapid injection into a primary nanochannel 20, followed by a ~6-fold reduction in velocity upon passage through the region interfaced to the nanoscale manifold 32. FIG. 7B illustrates adjacent different DNA images (b), (c), (d). The bright-field microscope image of the device (b) shows the location of the primary nanochannel entrance and the junctions with the four nanoslits comprising the nanoscale manifold nearest to the entrance. The fluorescence image of a DNA molecule stained with an intercalating dye at image (c) shows the molecular conformation from a single video frame. The time series or kymogram (d) shows the position of the DNA molecule at multiple time points as it traverses the primary nanochannel. This time series reveals the rapid transport of the DNA molecule in the initial region of the primary nanochannel. In each of the nanochannel segments of the transport channel 20 located between a pair of manifold nanoslits 31, the molecule's velocity is decreased. This stepwise reduction results in the apparent curvature in the region demarcated by dashed lines in (image (d)) of FIG. 7B. A lower, nearly constant velocity characterizes the subsequent transport of the DNA molecule.

Figure 8A:
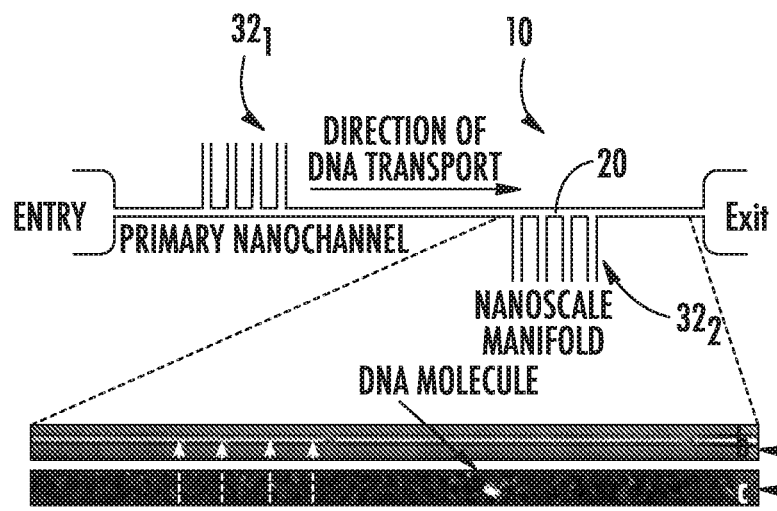
FIG. 8A is schematic illustration of a fluidic analysis device with a nanoscale manifold configured to increase the velocity of molecular transport in a primary transport nanochannel (indicating the direction of transport of a DNA molecule) according to embodiments of the present invention.
Figure 8B:
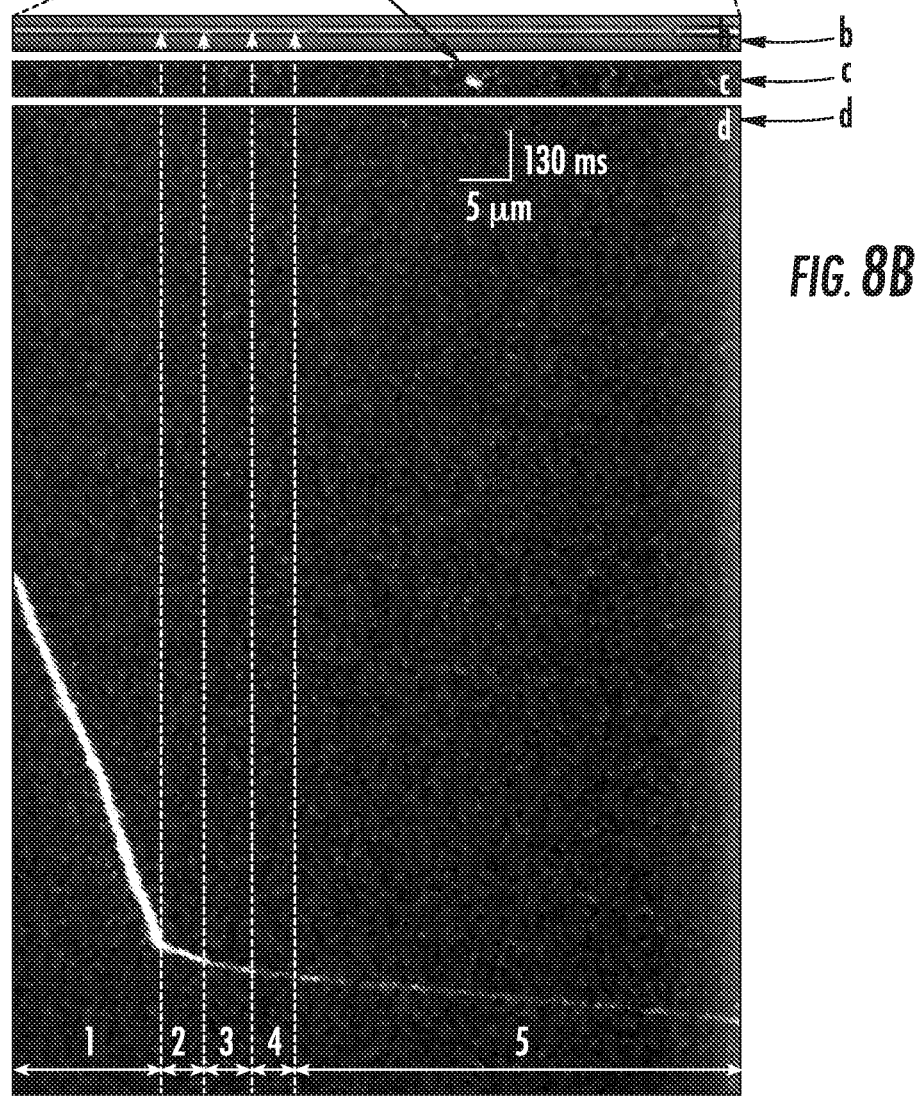
FIG. 8B shows adjacent images/panels (b), (c) and (d) of the transport nanochannel shown in FIG. 8A with a 10 kbp long DNA molecule stained with intercalating fluorescent dye according to embodiments of the present invention. Image (b) is a bright-field micrograph showing the entry region, the primary nanochannel and the manifold nanoslits. Image (c) is a representative fluorescence image of a DNA molecule in the primary nanochannel Image (d) is a kymogram (images recorded at 330 frames/second) showing the change in the DNA molecule's position over time as it is driven through the primary transport nanochannel. The position of the nanoslits in FIG. 8B are indicated by the vertical broken lines.

FIGS. 8A and 8B illustrate the use of a nanoscale manifold 32 to increase the velocity of molecular transport within a primary nanochannel 20. In this example the analyte is a 10-kbp long DNA molecule stained with an intercalating fluorescent dye. FIG. 8A is a schematic of the device used to collect the data shown in FIG. 8B. In FIG. 8B, image (b) is a bright-field micrograph showing the primary nanochannel and a second set of manifold nanoslits. Image (c) is representative fluorescence image of a DNA molecule in the primary nanochannel. Image (d) is a kymogram (images recorded at 330 frames per second) showing the change in the DNA molecule's position over time as it is driven through the primary transport nanochannel. The positions of the manifold nanoslits are indicated by the dashed lines. The molecule is initially driven through the primary nanochannel (segment 1 in panel (d) by a 32.7 V/cm magnitude electric field. The field strength in the primary channel is gradually increased by the action of the nanoscale manifold to the following values in each of the segments numbered in panel (d): 2, 127.2 V/cm; 3, 230.8 V/cm; 4, 350.7 V/cm; 5, 495.5 V/cm. The total relative increase in velocity is 15.13-fold.

FIG. 8A shows the same device 10 as in FIG. 7A but operated differently as noted above. FIG. 8B illustrates adjacent different images (b), (c), (d). Image (b) shows the location of the primary nanochannel exit end and the junctions with the four nanoslits comprising the nanoscale manifold. The fluorescence image of a DNA molecule stained with an intercalating dye per image (c) shows the molecular conformation from a single video frame, while the time series or kymogram (image (d)) shows the position of the DNA molecule at multiple time points as it traverses the primary nanochannel. This time series reveals the relatively slow transport of the DNA molecule in the initial region of the primary nanochannel shown in the figure. In each of the transport nanochannel segments located between a pair of manifold nanoslits 31, the molecule's velocity is increased. This stepwise increase results in the apparent curvature in the region demarcated by dashed lines in image (d) of FIG. 8B. Transport of the molecule in the rightmost segment of the primary nanochannel, after (to the right of) the nanoscale manifold, is characterized by the molecule's relatively high, constant velocity. Overall the DNA velocity increased ~15-fold as it moved from left to right through the second manifold region.

The behavior of the device 10 that is shown in FIGS. 7A and 8A (representative of a class of devices shown schematically in FIG. 1A) was characterized for a wide range of molecule deceleration and acceleration conditions that were controlled by the input voltages driving electrokinetic DNA transport. For each condition, the electric field strength in each segment of the primary transport nanochannel was estimated from the equivalent circuit shown in FIG. 1C, where the resistances were the resistances to the ionic current in the electrolyte solution calculated from the dimensions (width, depth, length) of each segment of the primary nanochannel and each nanoslit in the nanoscale manifolds. DNA velocity in each segment of the primary nanochannel was determined from fluorescence images in time series similar to those shown in FIGS. 7B and 8B (image (d)).

Figure 9:
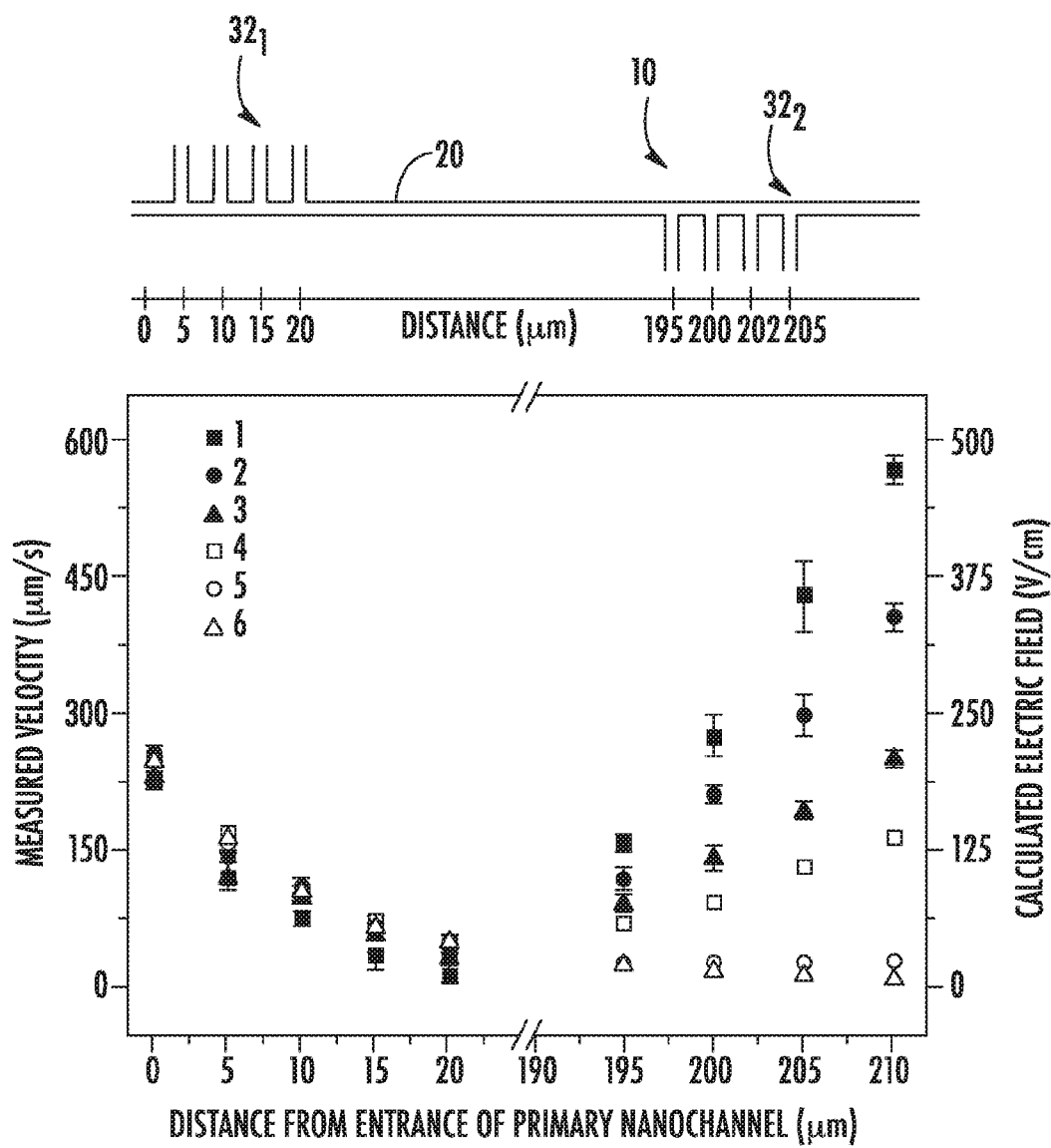
FIG. 9 is a plot of velocity (μm/s) and calculated electric field (V/cm) versus distance from entrance of the primary nanochannel (μm) for six different experimental conditions showing the tunability of analyte transport velocity using one or more nanoscale manifolds interfaced to the primary transport nanochannel according to embodiments of the present invention.

FIG. 9 shows how the DNA velocity was affected at various positions along the primary nanochannel 20 in each of the six experiments. These experiments varied the four input voltages such that DNA molecules experienced comparable deceleration after entry into the primary nanochannel in each of the experiments. In each experiment, however, DNA molecules experienced significantly different degrees of acceleration near the exit (right) end of the primary nanochannel. Thus, the plot/graph in FIG. 9 shows the tunability of analyte transport velocity. The velocities of 10-kbp DNA molecules were measured from kymograms such as those shown in FIGS. 7B and 8B. The average velocity of several molecules was determined within each segment of the primary transport nanochannel. In this demonstration, the entry electric field strength and the initial deceleration of the molecules were fixed for six different experimental conditions (different voltages applied to the primary nanochannel ends and to the two nanoscale manifolds). The change in velocity of the molecules at the exit end of the primary nanochannel was different for each of the experiments. The relative change in a DNA molecule's velocity was 15.1× for condition 1, 10.6× for condition 2, 6.2× for condition 3, 3.2× for condition 4, 1× for condition 5, and 0.5× for condition 6.

Figure 10:
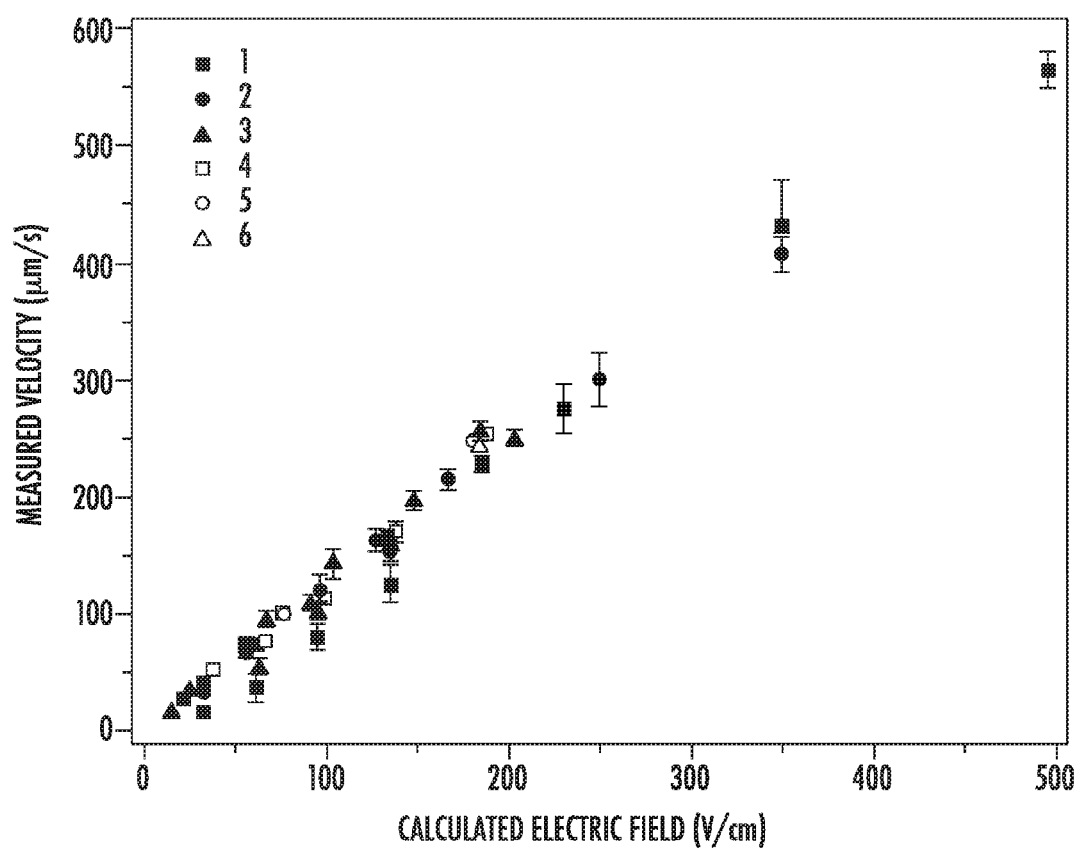
FIG. 10 is a graph of measured velocity (μm/s) versus calculated electric field (V/cm) showing characteristics of voltage-controlled transport of analyte molecules through a primary nanochannel for six different experimental conditions according to embodiments of the present invention.

FIG. 10 shows these same measured velocities as a function of the electric field strength estimated for each segment of the primary nanochannel using an equivalent circuit diagram. The linear dependence of velocity on estimated electric field strength indicated that interfacial effects or local perturbations to molecular conformations did not strongly affect DNA mobility under the conditions investigated. The plot/graph in FIG. 10 shows the characteristics of voltage-controlled transport of analyte Molecules through a primary transport nanochannel. Transport velocities of 10-kbp DNA molecules were measured under six different experimental conditions in the various segments of the primary transport nanochannel. The linear dependence of transport velocity on electric field strength indicates that a similar electrophoretic mobility is measured in each experiment [$1.2(\pm 0.2) \times 10^{-4}$ cm$^2$ V$^{-1}$ s$^{-1}$]. Deviation from linearity (most evident for data collected under experimental condition 1, black squares) is believed to be the result of pressure gradients established by high electro-osmotic flow rates under these experimental conditions.

Figure 11:
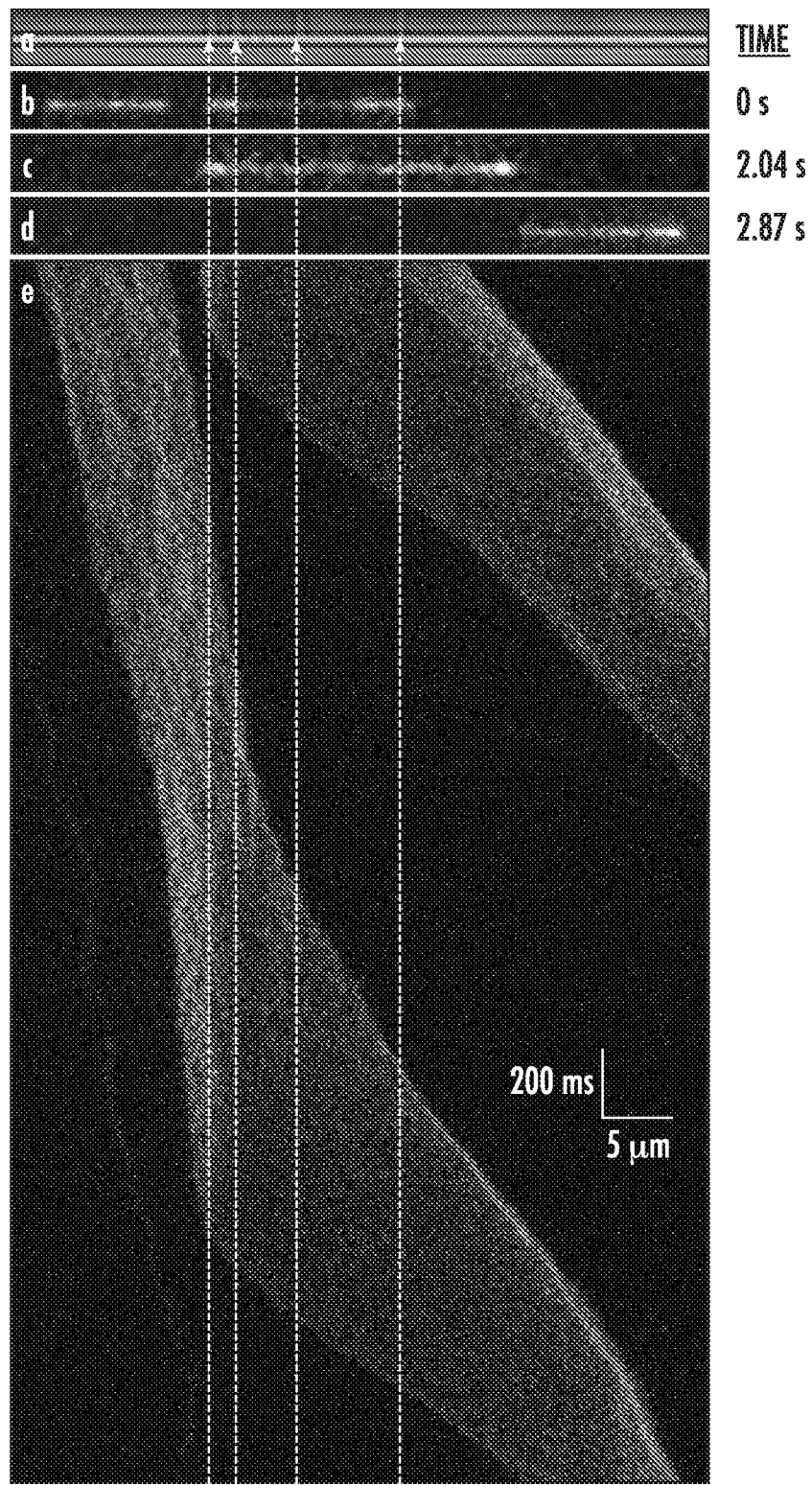
FIG. 11 shows adjacent images/panels (a), (b), (c), (d) and (e) of a device with a nanoscale manifold operated in an accelerating capacity to transport fluorescently stained T4-phasge DNA molecules (165 kbp, with a fully extended length of 73 μm) in a primary transport nanochannel. Image (a) is a bright-field micrograph of a portion of the device. Image (b) is a representative fluorescence image of two T4-phage DNA molecules in the primary nanochannel (the leftmost molecule is approaching the nanoscale manifold and the rightmost molecule spans the manifold). Image (c) is a representative fluorescence image of the leftmost molecule in (b) as it is stretched in the region of the nanoscale manifold. Image (d) is a representative fluorescence image of the molecule in (c) after it has exited the region of the manifold. Image (e) is a kymogram (images collected at 252 frames/second) showing the change in the DNA molecule's position over time as it is driven through the primary transport nanochannel. The position of the nanoslits of the manifold are indicated by the vertical broken lines.

Representative devices were also used to control the transport of long (>50 µm or >120 kbp) macromolecules. T4-phage DNA molecules (165-kbp long) have a fully extended length (73 µm) exceeding the total widths of the nanoscale manifolds (15 µm) on this device. Because the analyte macromolecule spanned multiple sections of the primary transport nanochannel having different electric field strengths, the nanoscale manifolds could be used to not only alter the overall velocity of the molecule's transport but also affect molecular compression and stretching (FIG. 11). The device used to collect these data employed nanoscale manifold elements with a staggered spacing (indicated by the vertical dashed lines in FIG. 11), in contrast to the evenly spaced manifold elements of the device shown in FIGS. 7 and 8. FIG. 11 illustrates device performance for large DNA molecules. Fluorescently stained T4-phage DNA molecules (165 kbp, with a fully extended length of 73 µm) are transported across a nanoscale manifold operated in an accelerating capacity. These molecules are long enough to span the entire width (15 µm) of the manifold during transit. Image (a) is a bright-field micrograph of the device. Image (b) is a fluorescence image of two T4-phage DNA molecules. The leftmost molecule has not yet reached the nanoscale manifold while the rightmost molecule spans the manifold. Image (c) is a fluorescence image of the leftmost T4-phage DNA molecule as it is stretched in the region of the nanoscale manifold. Image (d) is a fluorescence image of the leftmost T4-phage DNA molecule after it has exited the region of the nanoscale manifold. As it continues transport down the primary nanochannel, the tension imparted on the molecule by its passage through the accelerating region relaxes and the molecule's end-to-end length decreases. Image (e) is a kymogram (images collected at 252 frames per second) showing the entire transport process for the two molecules. The positions of the manifold elements (here nanoslits) are indicated by the dashed lines.

Figure 12:
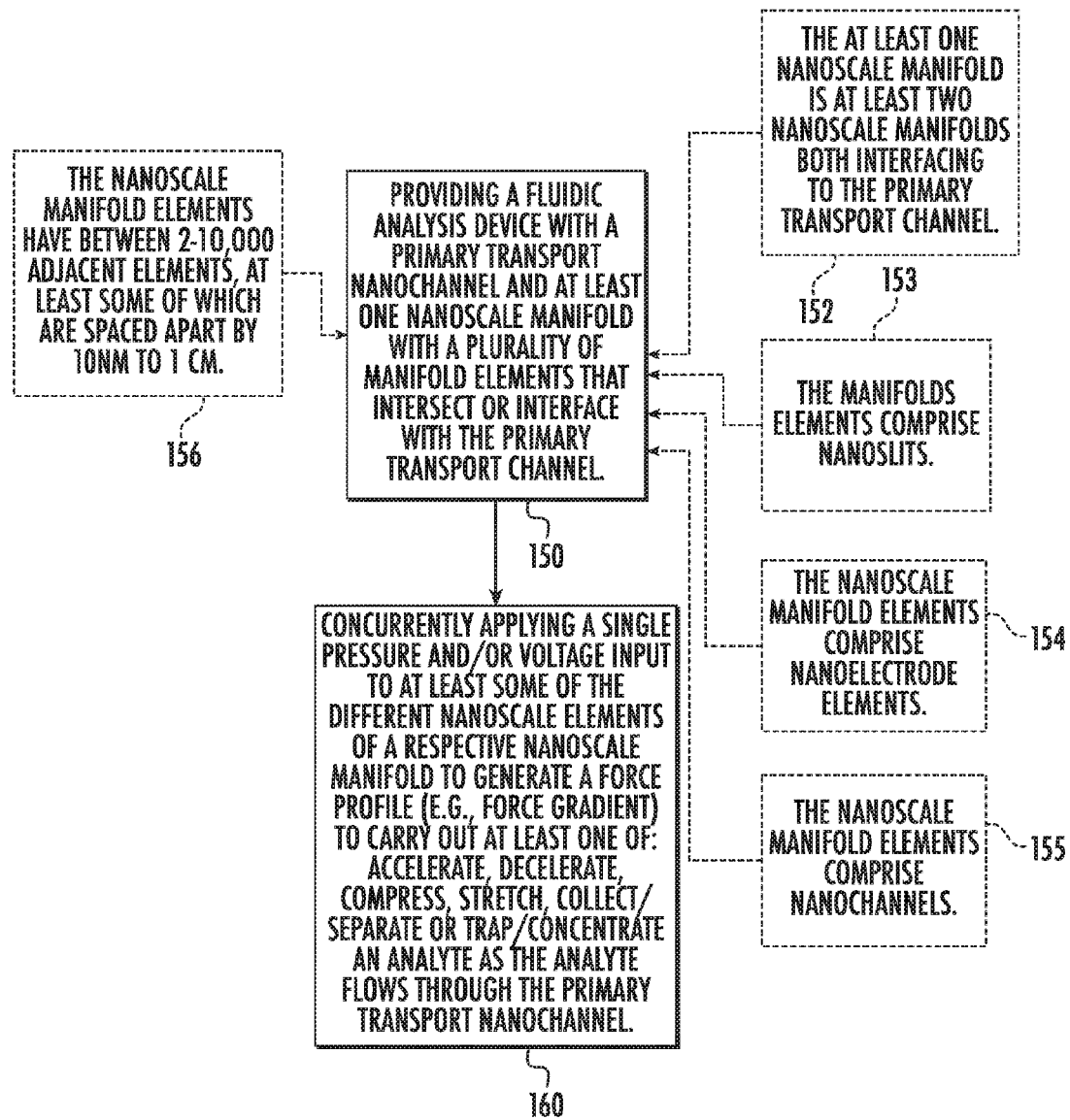
FIG. 12 is a flow chart of methods of operating a fluidic analysis device according to embodiments of the present invention.

FIG. 12 is a flow chart of exemplary actions that can be used to operate a fluidic analysis device. A fluidic analysis device is provided, the device having a primary transport nanochannel and at least one nanoscale manifold with a plurality of nanoscale manifold elements that intersect or interface with the primary transport channel (block 150). A single pressure and/or voltage input is concurrently applied to at least some of the different nanoscale elements of a respective nanoscale manifold to generate a force profile (e.g., force gradient) to carry out at least one of: accelerate, decelerate, compress, stretch, collect/separate or trap/concentrate an analyte as the analyte flows through the primary transport nanochannel (block 160).

The at least one nanoscale manifold can be at least two nanoscale manifolds (block 152). The nanoscale manifold elements can comprise nanoslits (block 153). The nanoscale manifold elements can comprise nanoelectrode elements (block 154). The nanoscale manifold elements comprise nanochannels (block 155).

The nanoscale manifold elements can have between 2-10,000 adjacent elements, at least some of which are spaced apart by 10 nm to 1 cm (block 156). The manifolds can have between 2-10, between 10-100, between 100-1000, between 1000-10,000 (or even more depending on the application).

The nanoscale manifolds 32 can allow the generation of a wide variety of precisely controlled force gradients using only a few input forces. The manifolds 32 can generate distributed force gradients (e.g., a force profile $P_F$) as opposed to large discrete changes in force magnitudes using a cross-channel, for example, and the ability to generate these gradients without relying on independent voltage or pressure control for each control element that intersects the primary transport nanochannel or nanochannel array. Gradients can be achieved over an arbitrarily large number of nodes (intersections between the primary transport nanochannel(s) and the nanoslits, nanochannels, or nanoelectrodes of a nanoscale manifold). This is believed to provide an unprecedented ability to establish user-defined force gradients, thereby affording control in each segment of the primary nanochannel(s) over the transport of analytes ranging from small molecules to centimeters-long stretched macromolecules.

Nanoscale manifolds have additional benefits for the manipulation of analyte molecules. In devices in which a single control nanoslit or nanochannel intersects the primary transport nanochannel(s), the degree to which the velocity of the molecule can be altered may be limited. Examples of fluidic devices with primary transport nanochannels are described in U.S. patent application Ser. No. 14/190,520, the contents of which are hereby incorporated by reference as if recited in full herein. Overaggressive attempts to alter the velocity with a single control nanoslit or nanochannel can result in the molecule's entry into the control structure, as opposed to the continued transport down a primary nanochannel. In a device containing a nanoscale manifold, in contrast, the gradual variation of the forces driving molecular transport can minimize the likelihood of transport down one of the nanoscale manifold elements. As illustrated in FIGS. 3A-F, 4, 5 and 6, there are a large number of design parameters that can be varied to engineer the desired device performance. Design choices can affect the shape of the force gradients, their sensitivity to the control voltages or pressures, and the range of control settings over which the device can be stably operated. Each of the aforementioned characteristics contributes to the tunability of the device performance. Nanoscale manifolds can be considered as modular elements, enabling several to be linked together to create complex, sometimes repeating force profiles to drive molecular transport. The control forces applied to the device may be held at constant values throughout operation or they may be varied in time, (e.g., stepped to different voltages or pressures, transiently pulsed to different voltages or pressures, continuously ramped at various linear or non-linear rates, varied according to a sinusoidal or other wave function). This possibility provides greater opportunities for complex transport control. Furthermore, nanoscale manifolds enable a small number of time-varying control forces to impact a large number of nodes in the primary transport nanochannel or nanochannel array with precisely controlled cooperative timing at each node.

Nanoscale manifolds have extremely broad applicability and can be integrated into a variety of nanofluidic devices in which a high degree of control over the transport of analyte molecules is desired. Devices can incorporate such manifolds to facilitate the analysis of polynucleic acids such as RNA and DNA. Possible applications include optically or electrically characterizing nucleic acids, assessing nucleic acid samples for polydispersity, mapping the positions of specific sequences, assessing environmentally caused damage, quantifying epigenetic modifications, quantifying protein binding, determining the secondary structure of single-stranded nucleic acids or single-stranded regions of nominally double-stranded nucleic acids, directly reading genomic sequence at single-nucleotide resolution, and identifying pathogens based on nucleic acid characterization. In other implementations the ability to hydrodynamically or electrostatically stretch macromolecules can be used to characterize proteins at the single-molecule level, mapping protein structure or locating the positions of enzyme active sites. More generally, such devices can be used to conduct force-response characterizations of any macromolecule, biological or synthetic. The electrophoretic mobility of denatured or native proteins within primary nanochannels can be measured to characterize a mixture of proteins. The ability to apply large forces at the primary nanochannel entrance facilitates high throughput operation while the ability to decrease analyte velocity within the nanochannel allows more sensitive detection of sample components.

Devices with nanoscale manifolds may facilitate the analysis of sample mixtures, either using single molecule sorting or sample preconcentration followed by ensemble separation techniques. As noted above, analytes of interest in such applications include small molecules, nucleic acids, proteins, peptides, polysaccharides, viruses, ribosomes, micelles, and nanoparticles, for example. The ability to characterize and controllably transport nucleic acids to various reservoirs using nanochannel devices could also be useful for pooling genomic elements for assembly into synthetic genomes.

Where multiple nanoscale manifolds 32 are used for a respective primary transport nanochannel 20, each bank or series of nanoscale elements 31 and/or nodes 31$n$ can allow precise and active control over the forces driving molecular transport in the various regions of the primary nanochannel(s). This allows for control over the transport of molecules along discrete regions of the primary nanochannel(s) 20. The manifold structures, such as those described, permit the establishment of designed monotonic force gradients along the length of the primary fluidic nanochannel(s) while limiting the required number of independent input potentials or pressures applied to the device. These tunable force gradients make the structures ideal for the manipulation of small molecules and macromolecules spanning many orders of magnitude in size while minimizing the occurrence of force gradient induced molecular fragmentation. Through the decoupling of the force magnitudes required to capture and then transport molecules through a nanochannel, precise spatio-temporal control over the molecules is obtained.

Fluidic devices 10 can be fabricated in a variety of substrates including silicon, glass (silica), quartz, plastics, thermoplastics, and elastomers or a combination thereof. Various nanopatterning methods known to those of skill in the art can be used independently or in combination to form the nanoscale features, such as high resolution photolithography, electron beam lithography, focused ion beam (FIB) milling, nanoimprint lithography, templating or molding strategies, wet or dry etching, molding, embossing, or machining. See, e.g., Guo L. J.; Cheng, X.; Chou C.-F. Fabrication of size-controllable nanofluidic channels by nanoimprinting and its application for DNA stretching. *Nano Lett.* 2004, 4, 69; WO2013/119765 and US2014/0360877; and WO2013/195723, the contents of which are hereby incorporated by reference as if recited in full herein. See also, Mijatovic, D.; Eijkel, J. C. T.; van den Berg, A. Technologies for nanofluidic systems: top-down vs. bottom-up—a review. *Lab Chip* 2005, 5, 492-500; Perry, J. L.; Kandlikar, S. G. Review of fabrication of nanochannels for single phase liquid flow. *Microfluid. Nanofluid.* 2006, 2, 185-193; Chantiwas, R. et al. Flexible fabrication and applications of polymer nanochannels and nanoslits. *Chem. Soc. Rev.* 2011, 40, 3677-3702; and Utko, P.; and Persson, F.; Kristensen, A.; Larson, N. B. Injection molded nanofluidic chips: Fabrication method and functional tests using single-molecule DNA experiments. *Lab Chip* 2011, 11, 303-308. The contents of which are hereby incorporated by reference as if recited in full herein. The ability to use wafer-scale processing can provide for a high impact, low cost technology.

Once the nanoscale and microscale elements are fabricated in the top surface of the substrate, a cover plate can be attached, typically bonded to the substrate to form the enclosed fluidic network using, for example, fusion bonding, anodic bonding, or bonding with an adhesive film between the bottom substrate and cover plate. The microchannels can be accessed through vias that pass through the bottom substrate and/or top cover plate.

Figure 13:
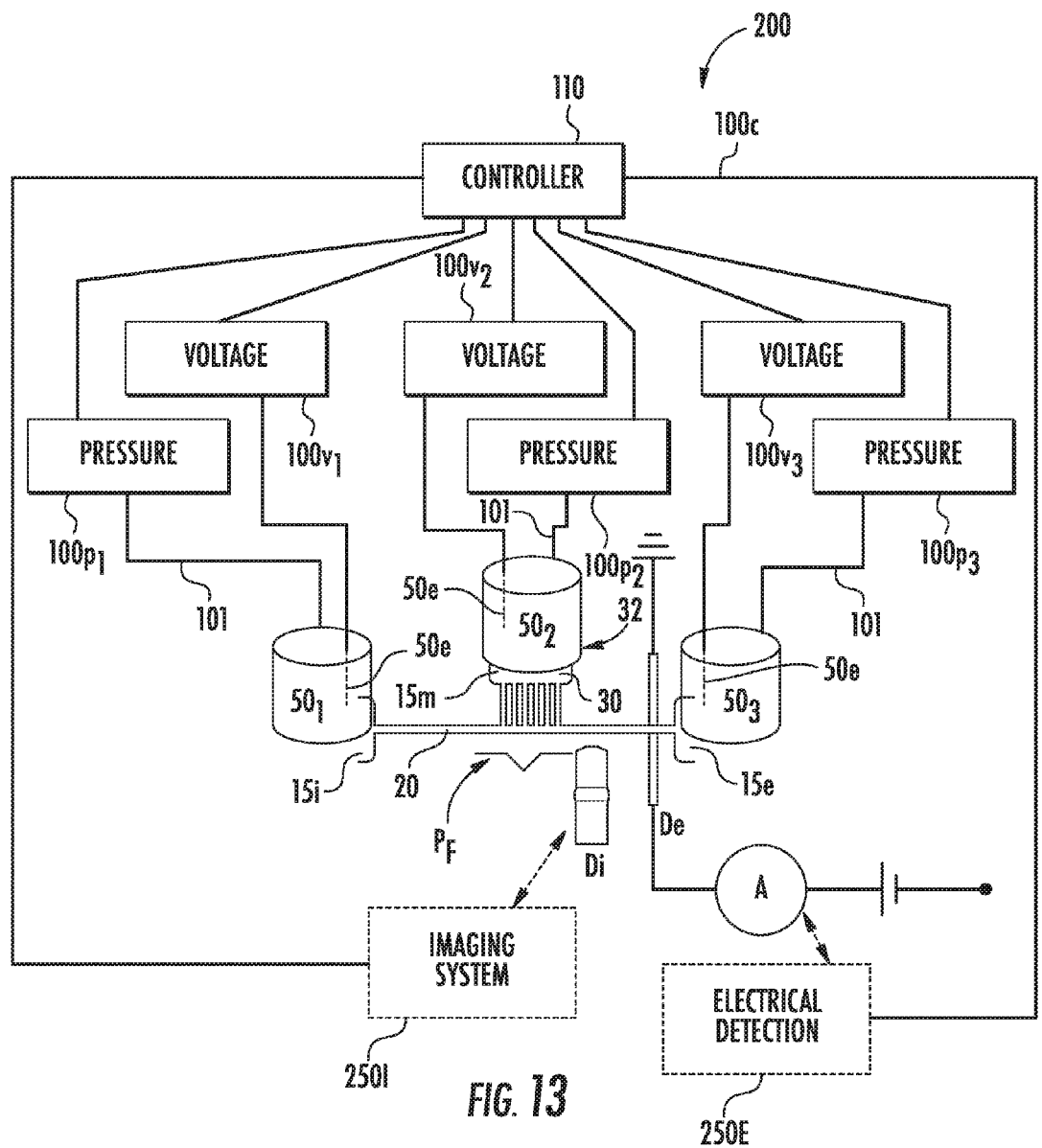
FIG. 13 is an example of a fluidic analysis system according to embodiments of the present invention.

Referring to FIG. 13, the system 200 can include a voltage input 100$v$ (shown as three independent voltage sources/power supplied) 100$v_1$, 100$v_2$, 100$v_3$ and/or a pressure input 100$p$ (shown as three independent pressurized gas supplies 100$p_1$, 100$p_2$, 100$p_3$ and respective supply lines 101), one each for a respective manifold 15$m$, an entrance end portion 15$i$ of a primary transport nanochannel 20 and an exit end portion of the primary transport nanochannel 20. One voltage and/or pressurized gas source 100$v_2$, 100$p_2$ can provide the input for the manifold reservoir 50$_2$ of a manifold junction 33 for the associated nanoelectrodes 31$e$ and/or fluidic elements 31$f$ (FIGS. 1A, 1B) for controllably applying voltage V and/or pressure P to achieve a force profile P$_F$ along the primary transport nanochannel 20 proximate the nanoscale manifold 32.

Reservoirs 50 (shown as 50$_1$, 50$_2$, 50$_3$) can be affixed to the device 10 to facilitate liquid handling. Input electrodes 50$e$ from a power source 100$v$ can be inserted into all or selected reservoirs 50. The reservoirs 50 have vias 50$v$. The input electrodes 50$e$ apply voltages across the various fluidic elements, e.g., transport channel ingress 15$i$, transport channel egress 15$e$, and manifold 32. Pressurized air or vacuum lines 101 can be coupled to the reservoirs 50 or vias to apply positive pressure or vacuum from the pressurized gas source 100$p$ to the fluidic elements and drive pressure-driven fluid flow. One or more reservoirs 50 can have both a pressurized gas/vacuum line 101 and an electrode input 50$e$.

The system 200 can have a circuit 100$c$ with at least one controller 110 that can apply the pressure and/or electrical input to a respective manifold 32 for the force profile P$_F$. The controller 110 can comprise at least one processor programmed to provide a menu of different operational timing diagrams and voltage/pressures for the force profile. The controller 110 can direct a desired voltage and/or pressure input timing program or algorithm that can also communicate with or includes a detection circuit with an optical and/or electrical detector Di, De associated with an imaging system 250I and/or electrical detection system 250E. The imaging system 250I can include the detector Di and an excitation source that can take a series of images of an analyte molecule in the detection channel. The imaging system 250 can be any suitable imaging system. The system 250 can include an excitation light source (typically for generating light that excites fluorescently labeled molecules) (which can optionally include a mirror, beam splitter, polarizer, lens, and/or other optical elements) and image generating device or detector D such as one or more of a camera, photomultiplier tube or photodiode. An objective/lens, where used, can reside under or over a primary surface of the transport channel of the device. The electric inputs/outputs and flow operation can reside on an opposing side of the device 10. The device 10 may also be flipped to operate on its side (with the flat primary surfaces being upright or angled) rather than substantially horizontal.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A fluidic device, comprising:
at least one fluidic transport nanochannel; and
at least one nanoscale manifold having a plurality of nanoscale elements, wherein the at least one nanoscale manifold comprises a first nanoscale manifold that extends from a single voltage and/or pressure input junction and is in fluid communication with a single manifold reservoir and comprises at least two of the nanoscale elements that directly interface with the at least one fluidic transport nanochannel, and wherein the at least two of the nanoscale elements of the first nanoscale manifold are configured to be concurrently controlled by a common externally applied pressure and/or voltage through the single voltage and/or pressure input junction to generate a force gradient within the at least one fluidic transport nanochannel,
wherein the at least one fluidic transport nanochannel comprises voltage and/or pressure input junctions that are separate from the single voltage and/or pressure input junction of the first nanoscale manifold, at least one accessing an entrance and at least one accessing an exit of the at least one fluidic transport nanochannel.

2. The device of claim 1, wherein the fluidic device is a chip, the device further comprising a plurality of reservoirs held by the chip, wherein the plurality of reservoirs includes the single manifold reservoir of the first nanoscale manifold, and wherein at least one reservoir of the plurality of reservoirs is in fluid communication with at least one microfluidic inlet or outlet to the at least one fluidic transport nanochannel and is spaced apart from the single manifold reservoir of the first nanoscale manifold.

3. The device of claim 1, wherein the at least one nanoscale manifold further includes a second nanoscale manifold with the first and second nanoscale manifolds both interfaced to at least a first one of the at least one fluidic transport nanochannel.

4. The device of claim 3, wherein the first nanoscale manifold is upstream of the second nanoscale manifold.

5. The device of claim 3, wherein the first nanoscale manifold faces the second nanoscale manifold across the first one of the at least one fluidic transport nanochannel.

6. The device of claim 1, wherein the plurality of nanoscale elements is between 2-10,000 adjacent nanoscale elements that directly interface with the at least one fluidic transport nanochannel, wherein at least some of the adjacent nanoscale elements are spaced apart by 10 nm to 1 cm.

7. The device of claim 1, wherein the plurality of nanoscale elements for a respective fluidic transport nanochannel is: (a) between 2-10, (b) between 10-100, (c) between 100-1000, or (d) between 1000-10,000.

8. The device of claim 1, wherein the nanoscale elements comprise nanoslits.

9. The device of claim 1, wherein the nanoscale elements comprise nanoelectrode elements.

10. The device of claim 1, wherein the nanoscale elements comprise nanochannels.

11. The device of claim 1, wherein the at least one nanoscale manifold comprises at least one cross-channel that connects at least two parallel nanoscale elements of the plurality of nanoscale elements that directly interface with at least one of the at least one fluidic transport nanochannel.

12. The device of claim 1, wherein the nanoscale elements include at least one diagonal nanoscale element.

13. The device of claim 12, wherein the at least one diagonal nanoscale element extends outward from at least one straight nanoscale element.

14. The device of claim 12, wherein the at least one diagonal nanoscale element extends from the single voltage and/or pressure input junction or channel segment associated therewith to the at least one fluidic transport nanochannel.

15. The device of claim 1, wherein the at least one fluidic transport nanochannel is a plurality of discrete, spaced apart fluidic transport nanochannels, and wherein the at least one nanoscale manifold interfaces with at least two of the plurality of fluidic transport nanochannels.

16. The device of claim 1, wherein the at least one nanoscale manifold interfaces with first and second spaced apart segments of at least one of the at least one fluidic transport nanochannel.

17. The device of claim 1, wherein the at least one fluidic transport nanochannel has a serpentine shape with first and second legs that are parallel, and wherein at least one of the at least one nanoscale manifold interfaces with both the first and second legs.

18. The device of claim 1, in combination with power and/or pressurized gas supplies and at least one controller in communication with the power and/or pressurized gas supplies, wherein each nanoscale manifold is controlled by a separate voltage and/or pressure input and is addressed individually, and wherein a single pressure and/or voltage input to a respective nanoscale manifold feeds only its respective nanoscale elements.

19. The device of claim 1, wherein each of the at least one nanoscale manifold resides on only one side of the at least one fluidic transport nanochannel.

20. The device of claim 1, wherein the force gradient generated within the at least one fluidic transport nanochannel is monotonic.

21. An analysis system, comprising:
(a) the fluidic analysis device of claim 1;
(b) a first power and/or first pressurized gas supply in communication with the single voltage and/or pressure input junction of the first nanoscale manifold to feed voltage and/or pressure to the nanoscale elements of the first nanoscale manifold so that the first nanoscale manifold applies a force gradient on an analyte in the at least one fluidic transport nanochannel; and
(c) at least one additional power and/or pressurized gas supply in communication with the voltage and/or pressure input junctions accessing the entrance and the exit of the at least one fluidic transport nanochannel,
wherein voltages and/or pressures applied by the at least one additional power and/or pressurized gas supply accessing the entrance and the exit of the at least one fluidic transport nanochannel and voltages and/or pressures applied by the first power and/or first pressurized gas supply to the first nanoscale manifold are independently controlled.

22. The system of claim 21, further comprising a controller in communication with the first and the at least one additional power and/or pressurized gas supply to independently control the applied voltages and/or pressures, wherein the at least one nanoscale manifold further includes a second nanoscale manifold spaced apart from the first nanoscale manifold and both the first and second nanoscale manifolds interface with at least one of the at least one fluidic transport nanochannel, and wherein each nanoscale manifold of the at least one nanoscale manifold has an independent pressurized gas supply and/or voltage input whereby each nanoscale manifold is independently addressable.

23. A fluidic device, comprising:
at least one fluidic transport nanochannel; and
at least one nanoscale manifold having a plurality of nanoscale elements, wherein the at least one nanoscale manifold comprises a first nanoscale manifold that extends from a single voltage and/or pressure input junction and is in fluid communication with a single manifold reservoir and comprises at least two of the nanoscale elements that directly interface with the at least one fluidic transport nanochannel, wherein the at least two of the nanoscale elements of the first nanoscale manifold are configured to be concurrently controlled by a common externally applied pressure and/or voltage through the single voltage and/or pressure junction to generate a force gradient within the at least one fluidic transport nanochannel,
wherein the at least one fluidic transport nanochannel further comprises a detection channel segment, and wherein the at least one fluidic transport nanochannel interfaces with the at least one nanoscale manifold upstream of the detection channel segment.

24. A method of controlling the transport of molecules within a fluid for the purposes of analysis, comprising:
providing the fluidic device of claim 1; and
automatically concurrently applying a single pressure and/or single voltage input to multiple nanoscale elements of a respective nanoscale manifold including the first nanoscale manifold to generate a force profile on the at least one fluidic transport nanochannel to carry out at least one of: accelerate, decelerate, compress, stretch, collect/separate or trap/concentrate an analyte as the analyte flows through the at least one fluidic transport nanochannel proximate the respective nanoscale manifold.

25. The method of claim 24, wherein the at least one nanoscale manifold is a plurality of nanoscale manifolds including the first nanoscale manifold and at least a second nanoscale manifold, each interfacing with at least one of the at least one fluidic transport nanochannel, and wherein each nanoscale manifold is independently controlled to apply a force gradient to a respective fluidic transport nanochannel.

26. The method of claim 24, wherein the nanoscale elements are fluidic nanoscale elements.

27. The method of claim 24, wherein the nanoscale elements comprise nanoelectrodes.

28. The method of claim 24, further comprising controlling molecular transport in the at least one fluidic transport nanochannel by selectively dynamically changing force gradients applied by the at least one nanoscale manifold.

29. The method of claim 28, wherein the controlling comprises changing the force gradient in one or more of magnitude, shape, and polarity using a single external voltage input and/or a single pressure input to a respective input junction of each of the at least one nanoscale manifold.

30. The method of claim 28, wherein the controlling comprises varying a single external voltage input and/or a single pressure input to single voltage and/or pressure input junction of the first nanoscale manifold in a time-dependent manner such as stepping to different voltages or pressures, transiently pulsing to different voltages or pressures, continuously ramping at various linear or non-linear rates, or varying according to a sinusoidal or other wave function.

* * * * *